United States Patent [19]

Belliotti et al.

[11] Patent Number: 5,356,898
[45] Date of Patent: Oct. 18, 1994

[54] SUBSTITUTED 4,6-DI-TERTIARY-BUTYL 5-HYDROXY-PYRIMIDINES

[75] Inventors: Thomas R. Belliotti, Phoenixville, Pa.; Catherine R. Kostlan, Saline; David T. Connor, Ann Arbor, both of Mich.

[73] Assignee: Warner-Lambert Company, Morris Plains, N.J.

[21] Appl. No.: 84,188
[22] PCT Filed: Jan. 17, 1992
[86] PCT No.: PCT/US92/00442
  § 371 Date: Jul. 1, 1993
  § 102(e) Date: Jul. 1, 1993
[87] PCT Pub. No.: WO92/13844
  PCT Pub. Date: Aug. 20, 1992

Related U.S. Application Data

[63] Continuation-in-part of Ser. No. 648,114, Jan. 31, 1991, abandoned.

[51] Int. Cl.⁵ ................. A61K 31/505; C07D 239/02
[52] U.S. Cl. ........................................ 514/269; 544/298
[58] Field of Search ........................ 544/298; 514/269

[56] References Cited

U.S. PATENT DOCUMENTS

| | | | |
|---|---|---|---|
| 4,711,888 | 12/1987 | Walker et al. | 514/269 |
| 4,859,679 | 8/1989 | Santini | 514/273 |
| 4,940,712 | 7/1990 | Walker et al. | 514/272 |
| 5,155,122 | 10/1992 | Connor et al. | 514/363 |
| 5,196,431 | 3/1993 | Belliotti et al. | 544/298 |
| 5,220,025 | 6/1993 | Belliotti et al. | 544/298 |
| 5,240,929 | 8/1993 | Connor et al. | 544/298 |
| 5,248,682 | 9/1993 | Connor et al. | 544/298 |

FOREIGN PATENT DOCUMENTS

| | | |
|---|---|---|
| 373827 | 6/1990 | European Pat. Off. |
| 1476534 | 5/1965 | France |

OTHER PUBLICATIONS

A. Sen et al., Indian Journal of Chemistry, vol. 24B pp. 535–538 (May 1985).
Bioch. J. 1951, 48, p. 400.
Effect of Structure on Potency and Selectivity in 2,6–Disubstituted 4–(2–Arylethenyl)Phenol Lipoxygenase Inhibitors E. Lazer, et al.–J. Med. Chem. 1990, 33, 1892–1898.
Derwent 89-167195/23 (1989) Abstract of EP 319170.
Derwent 87-236597/34 (1987) Abstract of EP 233461.
Derwent 89-309015/42 (1989) Abstract of US 4859679.
Derwent 85-312102/50 (1985) Abstract of EP 164204.
Derwent 89-295767/41 (Aug. 1989) Abstract of JP 1216978.
Derwent 46267C/27 (May 1980) Abstract of UK 2045756.
Chem. Ber. (1960) pp. 1998–2001 A. Dornow, et al.
Chemical Reviews 1975, vol. 75, No. 4, pp. 207 & 412.
J. C. S. Perkin I (1976) 1202–4, Roeterdink, et al.

Primary Examiner—Cecilia Tsang
Attorney, Agent, or Firm—Ronald A. Daignault; Charles W. Ashbrook

[57] ABSTRACT

The present invention is novel compounds which are 4,6-di-tertiary-butyl-5-hydroxy-1,3-pyrimidine substituted 1,2,4- and 1,3,4-thiadiazoles and oxadiazoles, and 1,2,4-triazoles, and pharmaceutically acceptable additions and base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever, and particularly rheumatoid arthritis, osteoarthritis, other inflammatory conditions, psoriasis, allergic diseases, asthma, inflammatory bowel disease, GI ulcers, cardiovascular conditions, including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. The preferred use is in treating inflammatory conditions. Thus, the present invention is also a pharmaceutical composition or method of manufacturing a pharmaceutical composition for the use of treating the noted conditions.

25 Claims, No Drawings

SUBSTITUTED 4,6-DI-TERTIARY-BUTYL 5-HYDROXY-PYRIMIDINES

CROSS-REFERENCE TO RELATED APPLICATIONS

This application is a continuation-in-part of U.S. application Ser. No. 07/648,114 now abandoned of Jan. 31, 1991, which was filed internationally thru the Patent Cooperation Treaty on Jan. 17, 1992 as PCT/US 92/00442.

BACKGROUND OF THE INVENTION

The present invention is novel compounds which are 4,6-di-tertiary-butyl-5-hydroxy-1, 3-pyrimidine substituted 1,2,4- and 1,3,4-thiadazoles and oxadiazoles, and 1,2,4-triazoles, and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever, and particularly rheumatoid arthritis, osteoarthritis, other inflammatory conditions, psoriasis, allergic diseases, asthma, inflammatory bowel disease, GI ulcers, cardiovascular conditions, including ischemic heart disease and atherosclerosis, and ischemia-induced cell damage, particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. The preferred use is in treating inflammatory conditions. Thus, the present invention is also a pharmaceutical composition or method of manufacturing a pharmaceutical composition for the use of treating the noted conditions.

3,5-Ditertiarybutyl-4-hydroxyphenyl substituted 1,2,4- and 1,3,4-thiadiazoles and oxadiazoles, and 1,2,4-triazoles are known to provide activity as inhibitors of 5-lipoxygenase and/or cyclooxygenase. See U.S. application Ser. No. 07/277,171, filed Nov. 29, 1988, now abandoned, and U.S. application Ser. No. 07/426,814, filed Oct. 30, 1989, now pending. Pyrimidine is not noted in this reference. Structure activity relationships of certain ditertiaryphenols and homologs thereof are discussed by Lazer, E. S., et al in "Effect of Structure on Potency and Selectivity in 2,6-Disubstituted 4-(2-Arylethenyl)phenol Lipoxygenase Inhibitors of *J. Med. Chem.* 1990, 33, 1892–1998. Again, pyrimidines are not noted in this reference and so compounds therein differ from the present invention.

Numerous references disclose 2-amino-5-hydroxy pyrimidines. Compounds having other N containing groups in place of the amino are also disclosed, however, in each such compound all attachments are through the N. Such disclosed pyrimidines may also be substituted at the 4- and/or 6-positions with various groups including alkyls. No reference shows a tertiarybutyl in both the 4- and the 6-positions in combination with a 5-hydroxy together with any group other than the N or S containing substituent in the 2-position as now found in the present invention. For example, UK patent application number 2045736 and the *Bioch. J.* 1951, 48, p. 400 shows the simple 2-amino-5-hydroxy-4,6-dimethylpyrimidine. Other substituted 2-aminopyrimidines are shown in European patent application numbers 89312736.5 and 86305466.4 (equivalent to U.S. Pat. No. 4,711,888), European publication numbers 319170, 233416, 164204, and U.S. Pat. Nos. 4,859,679 and 4,940,712.

Japanese Application No. 1,216, 978 discloses 2-arylpyrimidines but differs from the present invention, that requires the 4,6-ditertiarybutyl-5-hydroxy substituents.

The difficulty of accommodating steric hindrance in the synthesis of 4,6-ditertiarybutyl substituted pyrimidine N-oxide is documented in J. C. S. Perkin I (1976) 1202–4. No 5-OH is considered in this synthesis. Further, although French Application No. 1,476,534 presents a generic scope including various 2-substituted pyrimidines this French application differs from the present invention by failing to provide the present invention substituent combinations.

The disclosures in *Chem. Ber.* (1960), p. 1998–2001 and in *The Indian Journal of Chemistry*, Vol. 24B, May 1985, pp. 535–538, showing oxazole to pyrimidine ring transformations and the disclosure in *Chemical Reviews* 1975, Vol. 75, No. 4, pp. 207 and 412 showing a preparation of an oxazole and subsequent transformation to pyrimidine all show a synthesis and product having substituents in the 4- and 6-positions offering little or no steric hindrance contrary to the present invention which contains 4,6-ditertiarybutyl together with a 5-hydroxy substituent.

In summary, the references of record show neither the present 2-substituent nor combinations of 4- and 6-substituents with a 5-hydroxy group and particularly combinations in which the 4- and 6-substituents are ditertiarybutyl groups which provide steric hindrance during synthesis of pyrimidines.

In fact, there are numerous references showing 4,6-dimethyl-5-hydroxy-2-substituted pyrimidines.

Thus, the references of the prior art differ from that as set out in the present invention.

SUMMARY OF THE INVENTION

The present invention is a compound of the formula (I)

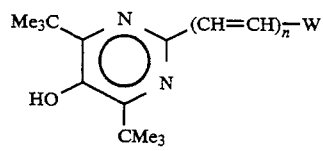

and a pharmaceutically acceptable acid addition or base salt thereof and hydrates; wherein n is zero or one, and W is

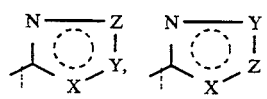

wherein X is N, $NR_1$, O, or S wherein $R_1$ is hydrogen or lower alkyl;

Z is O, S, $NR_1$ or N wherein $R_1$ is independently as defined above; with the proviso that when Z is $NR_1$ or N at the same time that X is N or $NR_1$ then X must be N when Z is $NR_1$ and X must be $NR_1$ when Z is N and also with the proviso that when X is S or O then Z must be N, and that when Z is S or O then X must be N, i.e. one of either X or Z must be N;

Y is (1) C—SR$_1$ wherein R$_1$ is independently as defined above (2) $\overset{O}{\underset{\|}{C}}$—SR$_2$ wherein R$_2$ is lower alkyl, (3) $\overset{O}{\underset{\|}{\underset{\overset{\|}{O}}{C}}}$SR$_2$ wherein R$_2$ is as defined above, (4) C—NR$_1$R$_3$ wherein R$_1$ is independently as defined above and R$_3$ is hydrogen or lower alkyl, (5) COR$_1$ wherein R$_1$ is independently as defined above, (6) CR$_4$ wherein R$_4$ is halogen, CF$_3$, CO$_2$R$_1$, or $\overset{O}{\underset{\|}{S}}$NHR$_1$, $-\overset{O}{\underset{\|}{C}}$—R$_7$, $\overset{S}{\underset{\|}{C}}$—R$_7$, $\overset{NR_1}{\underset{\|}{NHC}}$NR$_1$R$_3$, $\overset{S}{\underset{\|}{NHC}}$NR$_1$R$_3$, $\overset{O}{\underset{\|}{NHC}}$NR$_1$R$_3$, $\overset{O}{\underset{\|}{NR_1C}}$R$_5$, $\overset{S}{\underset{\|}{NR_1C}}$R$_5$, NHCN, HN$\overset{R_1}{\underset{}{\diagup}}$CO$_2$R$_1$, CH$_2$OR$_1$, NH$\overset{N-SO_2H_3}{\underset{}{\diagup\diagdown}}$NR$_1$R$_3$, NH$\overset{N-CN}{\underset{}{\diagup\diagdown}}$NR$_1$R$_3$, NH$\overset{C-NO_2}{\underset{}{\diagup\diagdown}}$NR$_1$R$_3$, NH$\overset{O}{\underset{\|}{S}}$R$_2$, NH$\overset{O}{\underset{\|}{\underset{\overset{\|}{O}}{S}}}$NR$_1$R$_3$, NR$_1$OR$_3$, S(CH$_2$)$_m$CO$_2$H, CN, NH(CH$_2$)$_m$OH, CCl$_3$, CONR$_1$R$_3$, CSNR$_1$R$_3$, CH$_2$X$_{10}$, CH$_2$NR$_{11}$R$_{13}$, NHCSNHCO$_2$R$_2$, CH$_2$SR$_2$, CH$_2$SO$_2$R$_2$, or NHNH$_2$, (7) C—N=C$\overset{\diagup OR_2}{\diagdown R_1}$, wherein m is 1, 2, or 3; R$_{11}$ and R$_{13}$ are hydrogen, lower alkyl or taken together with N form a saturated ring having from 4 to 6 carbons; X$_{10}$ is halogen or NO$_2$; R$_5$ is H, lower alkyl or OR$_1$; R$_7$ is lower alkyl, phenyl or CF$_3$; and R$_1$, R$_2$, and R$_3$ are independently as defined above. The most preferred compound of formula I is 5-[4,6-bis(1,1-dimethylethyl)-5-hydroxy-2-pyrimidinyl]-2-thiomethoxy-1,3,4-3H-thiadiazole.

The present invention is also a pharmaceutical composition for the treatment of conditions advantageously affected by the inhibition of 5-lipoxygenase and/or cyclooxygenase which comprises an amount effective for the treatment of the condition of a compound of the formula I and the pharmaceutically acceptable acid addition or base salt thereof together with a pharmaceutically acceptable carrier. The condition is meant to include, for example, arthritis or other inflammatory diseases, allergic diseases, pain, fever, and psoriasis, but preferably inflammatory diseases.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of medical therapeutic agent.

Pharmaceutical composition or use of the compound or salt of formula I is meant to include treatment understood to be prophylactic pertinent to the foregoing named condition.

Con, pounds of the formula I in this invention are inhibitors of the synthesis of the products of the enzymes 5-lipoxygenase and/or cyclooxygenase, and will be useful for the treatment of rheumatoid arthritis, osteoarthritis, other inflammatory conditions, psoriasis, allergic diseases, asthma, inflammatory bowel disease, GI ulcers, cardiovascular conditions, including ischemic heart disease and atherosclerosis, and ischemia-induced cell damage particularly brain damage caused by stroke. They can also be used topically for treating acne, sunburn, psoriasis, and eczema. Also included are leukotriene mediated pulmonary, gastrointestinal, inflammatory, dermatological, and cardiovascular conditions. The disclosed compounds also have potential utility as antioxidants. The preferred use is in treating inflammatory conditions.

Additionally, the present invention is a compound of the formula III

Q'Ar'Q"    III wherein Ar' is a group of the formula $$\text{Me}_3\text{C}-\overset{}{\underset{\text{Me}_3\text{C}}{\diagdown}}\text{(pyrimidine ring with 2 N)}\text{—}$$

Me i s CH$_3$;
Q' is hydrogen or a protecting group;
Q" is CHNOH, CN, CO$_2$H, CSNH$_2$, or $\overset{NH}{\underset{\|}{C}}$NHNH$_2$, CHO, COOR$_{20}$ wherein R$_{20}$ is lower alkyl.

Preferred species of formula III include:

4,6-Bis(1,1-dimethylethyl)-5-[(2-methoxyethoxy)methoxy ]-2-pyrimidine carbonitrile;

4,6-Bis(1,1-dimethylethyl)-5-hydroxy-2-pyrimidine carbonitrile;

4,6-Bis(1,1-dimethylethyl)-5-[(2-methoxyethoxy)methoxy ]-2-pyrimidine carboxaldehyde oxime;

4,6-Bis(1,1-dimethylethyl)-5-hydroxy-2-pyrimidine carboxaldehyde oxime;

4,6-Bis(1,1-dimethylethyl)-5-[(2-methoxyethoxy)methoxy ]-2-pyrimidinecarbothioamide; and 4,6-Bis(1,1-dimethylethyl)-5-hydroxy-2-pyrimidinecarbothioamide.

Activity for the use of the compounds of the present is found in 4,6-bis (1,1-dimethylethyl)-5-hydroxy-2-pyrimidine carbonitrile, The compounds of the formula III are useful as intermediates as shown in Scheme 1.

DETAILED DESCRIPTION OF THE INVENTION

In the compounds of formula (I) the term "lower alkyl" includes an alkyl group of from one to six carbons such as methyl, ethyl, propyl, butyl, and the like and isomers thereof. Halogen is chloro, bromo or fluoro.

The compounds I of the invention may exist as tautomers which are readily determined from art recognized tautomerism. Such tautomers are, for example, represented by formula I' and II" as follows:

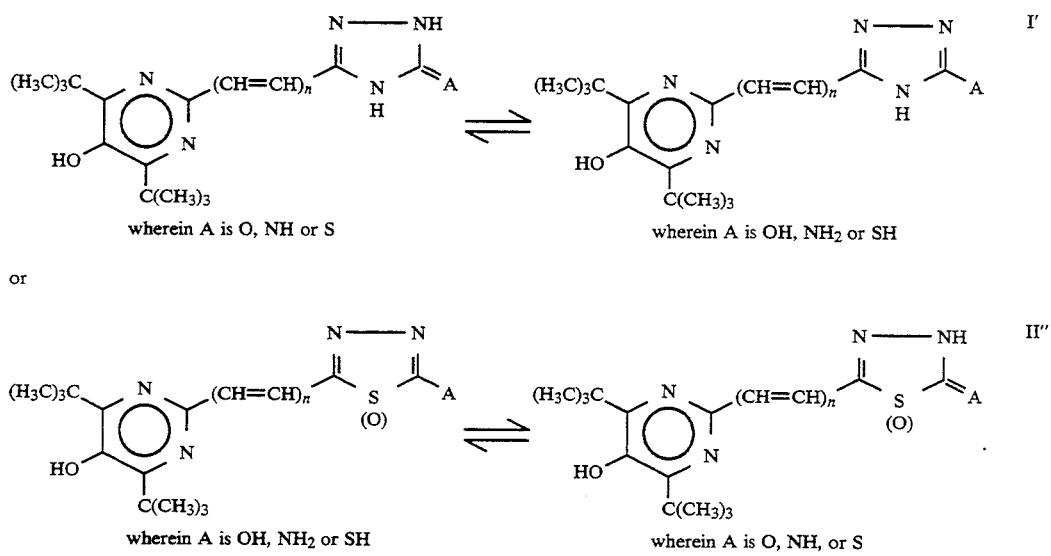

or

Appropriate compounds of formula (I) are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfamate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric or optical isomers. Thus, the invention includes the individual isomers and mixtures thereof. The individual isomers may be prepared or isolated by methods known in the art.

The compounds of the invention may contain an asymmetric carbon atom, particularly, for example, at the Y side chain of the compounds of formula I. Thus, the invention includes individual enantiomers, the pure S, the pure R isomer, and mixtures thereof. The individual enantiomers may be prepared or isolated by methods known in the art. Likewise diastereomers are included in the invention if possible, both as individuals or mixtures thereof.

Hydrates of compounds of formula I, if possible, are also the present invention and are prepared or isolated by conventional methods known to an ordinarily skilled artisan.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula (I) or pharmacologically acceptable salt thereof to achieve a therapeutic effect will, of course, vary both with the particular compound, the route of administration, the mammal under treatment, and the particular disorder or disease concerned. A suitable dose of a compound of formula (I) or pharmacologically acceptable salt thereof for a mammal suffering from, or likely to suffer from any condition as described hereinbefore is 0.1 µg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 µg of the compound per kilogram, typically about 0.1 µg/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2 \times 10^6$ cells/ml. Cells are incubated with and without test agent (in DMSO) (1% DMSO is without effect on arachidonic acid metabolism) for ten minutes at room temperature. Calcium ionophore A23187 (5 µM) is added and cells are incubated for seven minutes at 37° C. The reaction is stopped by chilling the tubes on ice for ten minutes. Cells are separated by centrifugation and the supernatant is stored at −20° Aliquots (100 µl) are analyzed for $LTB_4$ and $PGF_{2\alpha}$ using radioimmunoassay kits as provided by the supplier.

Biochemical data obtained from this whole cell assay may be shown as $IC_{50}$s which are calculated as the amount of test compound causing 50% inhibition of $LTB_4$ or $PGF_{2\alpha}$ formation.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 ml of sterile saline (0.9%) solution (Travenol). The solution is vortexed for 30 to 45 minutes. Animals are dosed with compound one hour before carrageenan challenge. Foot paw edema is induced by injecting 0.10 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the five-hour and the initial paw volume is expressed as delta edema. The delta edema for each test group of animals is used to calculate the percent inhibition of edema achieved by the compound at the test dose compared with the vehicle control group. The $ID_{40}$ (the dose at which swelling is inhibited by 40%) is calculated by probit analysis for the dose at which 40 percent inhibition occurs.

Mycobacterium-Induced Rat Footpad Edema Assay (MFE): Protocol

*Mycobacterium butyricum* (5 mg/ml) is suspended in paraffin oil by sonication for ten minutes in an ice bath. Footpad edema is induced on Day 0 by injecting 0.1 ml of the Mycobacterium mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle one hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis.

Gastric Ulcerogenicity (UD): Protocol

Male outbred Wistar rats (100–250 gms) are fasted for 24 hours. After fasting, test compounds are administered orally (in 2 ml/kg of 0.5% hydroxypropyl methylcellulose) and the rats are denied access to food and water for six more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the $UD_{50}$ (the dose which causes ulcers in 50% of the rats).

TABLE

| Example Number | ARBL | ARBC |
|---|---|---|
| 13 | 93% @ 10 μM | 85% @ 10 μM |
| 19 | 70% @ 10 μM | 45% @ 10 μM |

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen alumhum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH₃)COOH or —CH₂CH₂COOH group (which optionally can be in the form of a pharmaceutically acceptable salt group, e.g. , —CH(CH₃)COO⁻NA⁺ or —CH₂CH₂COO⁻Na⁺) , typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH₂COOH group (which optionally can be in the form of a pharmaceutically acceptable salt group, e.g. —CH₂COO⁻Na⁺) , typically attached directly to a ring system, preferably to an aromatic or heteroaromatic ring system.

The fenamic acid derivatives which may be used comprise: mefanamic acid, meclofenamic acid, flufenanlic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

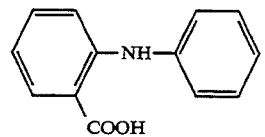

which can bear a variety of substituents and in which the free -COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

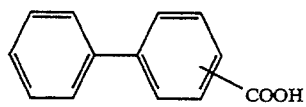

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

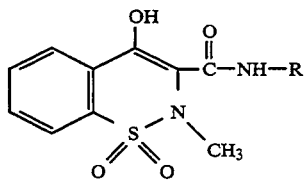

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflammizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an H₁ or H₂-receptor antagonist, such as for instance cimetidine, ranitidine, terrenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a K⁺/H⁺ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

In the following processes Ar=

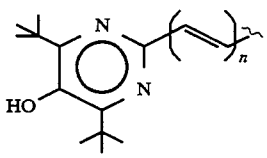

where n is 0 or 1.

Under certain circumstances as discussed below, it is necessary to protect the phenolic OH of Ar in various intermediates to give QAr where QAr is

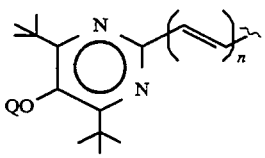

where Q is a suitable oxygen protecting group, preferably methoxyethoxymethyl (MEM) and where n=0 or 1.

The MEM group is removed later using 1) Lewis acids such as ZnBr₂ in halogenated solvents such as methylene chloride, chloroform, and dichloroethane at 0° to 60° C., 2) mineral acids such as HCl, HBr, or HNO₃ in solvents such as water, alkanols, tetrahydrofuran, dialkylethers, dioxane, glyme, diglyme at 0° to 60° C. or 3) organic acids such as acetic acid in the solvents described in 1) and 2) at 0° to 60° C.

Introduction and removal of such suitable oxygen protecting groups are well-known in the art of organic chemistry; see for example "Protective Groups in Organic Chemistry," J. F. W. McOmie, ed., (New York, 1973), pages 43ff, 95ff, J. F. W. McOmie, Advances in Organic Chemistry, Vol. 3, 159–190 (1963); J. F. W. McOmie, Chem. & Ind., 603 (1979), and T. W. Greene, "Protective Groups in Organic Synthesis", Wiley (New York) 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The starting materials for the present invention is prepared as set out below, and as repeated here from copending application PD-4176-01-JT.

Compound of the formula 3' in Scheme 1' below is prepared from the known haloketone 2' (C. W. Shoppee and D. Stevenson, *J. Chem. Soc. Perkin I*, p. 3015, 1972) by reaction with a salt of acetic acid such as sodium or potassium acetate in a solvent such as DMSO at a reaction temperature of 18° C. to 60° C., or in a solvent such as acetic acid at reflux. Acetoxydiketone 3' is converted to oxazole 4' by treatment with an ammonium salt such as ammonium chloride or preferably ammonium acetate in a solvent such as acetic acid at reflux for 1 to 16 hours or in a solvent such as formamide at 100° to 200° C. for 1 to 6 hours. Alternatively 2' is converted directly to 4' by treatment with acetamide or ammonium acetate in a solvent such as acetic acid at reflux. The oxazole 4' is converted to pyrimidine 5' by treatment with ammonia or an ammonium salt at elevated temperature. Preferably 4' is reacted with concentrated ammonium hydroxide at 150° to 190° C. in a pressure reaction vessel for 6 to 72 hours. 5' is also prepared by reaction of 3' with an ammonium salt such as $NH_4Cl$ or $NH_4OAc$ in a solvent such as formamide at a temperature of 180° to 200° C. for longer periods of time such as overnight to 1 week.

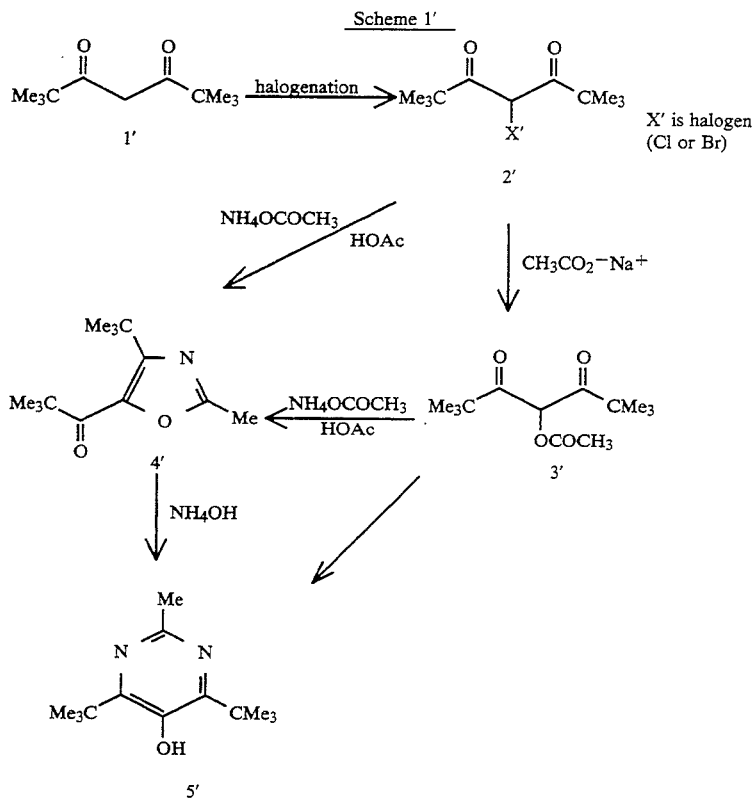

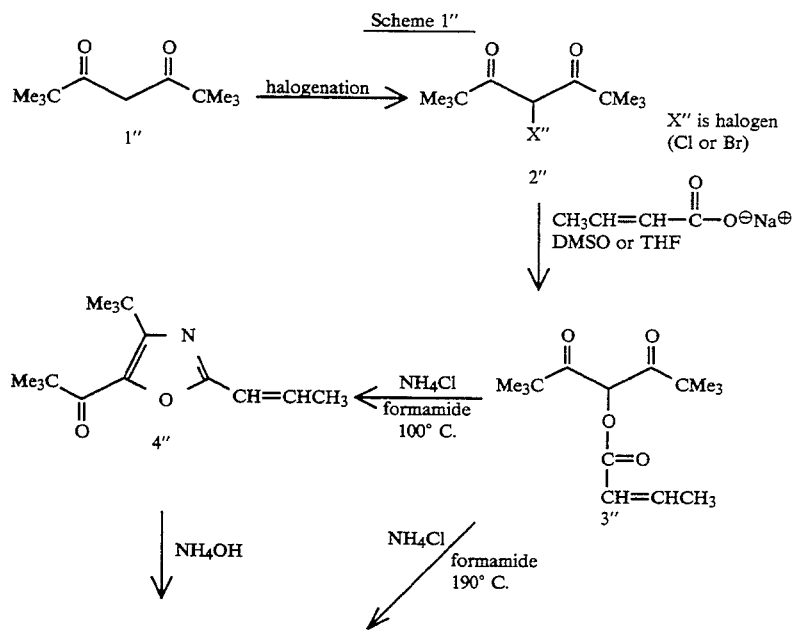

Scheme 1″

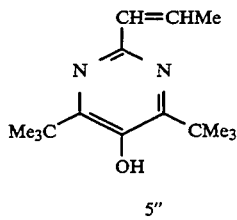

5″

Scheme 1″

By a method analogous to that shown in Scheme 1′, one would substitute appropriate reagents (Scheme 1″) to convert halodiketone 2″ to 5″. Preferred conditions for the conversion of halodiketone 2″ to 3″ are reaction of 2″ with the sodium salt of the appropriate carboxylic acid in a solvent such as DMSO or THF. The conversion of 3″ to 4″ is preferably carried out using ammonium chloride as the ammonium salt in formamide as the solvent.

Scheme 1‴

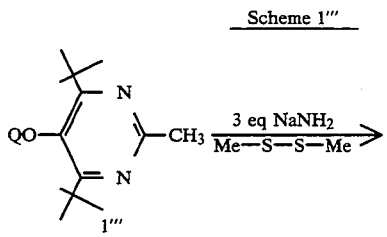

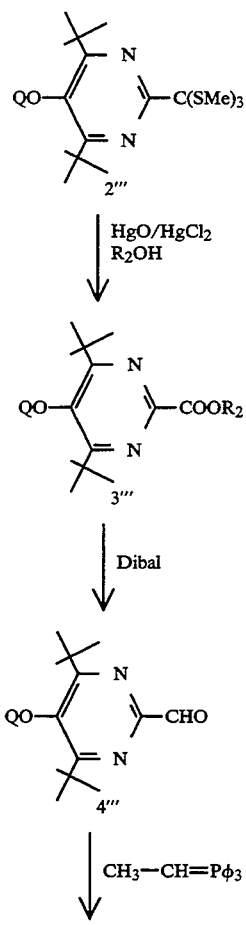

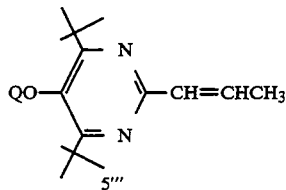

5‴

Scheme 1‴

Preferably, the intermediate olefin 5‴ is prepared in its protected form as shown in Scheme 1‴. Reaction of the O-protected 2-methyl pyrimidine 1‴ with 3 equivalents of sodium amide in liquid ammonia followed by the addition of dimethyldisulfide gives the orthoester 2‴. Treatment of 2‴ with mercuric chloride in an alcohol solvent gives the ester 3‴ which may be reduced with a reagent such as DIBAL to give the intermediate aldehyde 4‴. Wittig reaction on the protected aldehyde gives the O-protected intermediate 5‴.

The method of preparation for compounds 7, 8, and 9 in Scheme 1 from compound 1, where n=0, are illustrated below. The phenolic OH of the nitrile 1, prepared as shown and discussed below, is protected to give 2 using Q halogen wherein Q is a protecting group, preferably MEMCl, in the presence of bases such as trialkylamines and alkalihydrides in ether solvents such as diethyl ether, diisopropylether, t-butylmethylether, tetrahydrofuran, dioxane, glyme or diglyme; or chlorinated solvents such as dichloromethane, chloroform, dichloroethane, or carbon tetrachloride; or aromatic solvents such as benzene, toluene, xylene, mesitylene or chlorinated benzenes at −10° to 200° C. for up to 5 days. Alternatively, compound 2 is prepared from the protected 2-methylpyrimidine 10 by nitrosation in the presence of a strong base such as sodium amide in ammonia at a temperature of −78° C. to the reflux temperature of ammonia or butyllithium in a solvent such as THF at −78° C. to 0° C. using a nitrosating reagent such as an alkylnitrite such as isoamylnitrite or t-butylnitrite. The resulting oxime 11 may be dehydrated to the protected nitrile 2 by a reagent such as DMF/oxalyl chloride at temperatures such as −78° C. or may be dehydrated and deprotected in one step to 1 in the case of acid-sensitive protecting groups at higher temperatures. Compound 2 is treated with NaNHNH$_2$, LiNHNH$_2$ or KNHNH$_2$ to give amidrazone 3 in ether solvents at 0° to 60° C. The reaction of amidrazone 3 with 1,1-carbonyldimidazole, phosgene, diphosgene or triphosgene in the presence of trialkylamines in ether solvents or chlorinated solvents at 0° to 200° C. for up to 5 days gives triazolone 4. In a similar manner, compound 5 is prepared from 3 using 1,1-thiocarbonyldiimidazole or thiophosgene as reagents. Compound 6 is prepared from 3 using carbon disulfide in chlorinated or aromatic or ether solvents or alkanols at 0° to 200° C. for up to 5 days. Compounds 4, 5, and 6 are deprotected as described above to give 7, 8 and 9.

Alternatively, protected nitrile 2 may be reacted with H$_2$S in a solvent such as triethylamine or pyridine to give an intermediate thioamide which is in turn converted to amidrazone 3 by reaction with hydrazine in a suitable solvent such as methanol.

Alternatively, protected nitrile 2 may be converted to the corresponding aldehyde 12 by methods well known in the art. The aldehyde 12, when n=0, may be reacted with the appropriate Wittig reagent to give compound 10 where n=1 or with the appropriate Wittig reagents to give 1, 13, or 12 where n=1. Additionally, aldehyde 12 may be used in Knoevenagel condensations, for example, with 2-(5-oxo-4,5-dihydro- 1H-1,2,4-triazolyl-3-yl)acetic acid to triazolone 7 where n=1.

for up to 5 days. In addition, R$_2$ in compound 2 is defined as K$^+$ or Na$^+$ or Li$^+$ to give 4 where R$_2$ is transformed to H after treatment with acid. Treatment of 3 with acid, such as aryl sulfonic acids or alkylsulfonic acids or mineral acids, in chlorinated or aromatic or ether solvents at 0° to 150° C. for up to 5 days gives 4. Compound 5 is prepared from 4 using sodium or lithium or potassium alkythiolates, or KCN, NaCN in DMF at 0° to 150° C. for up to 5 days.

Scheme 2

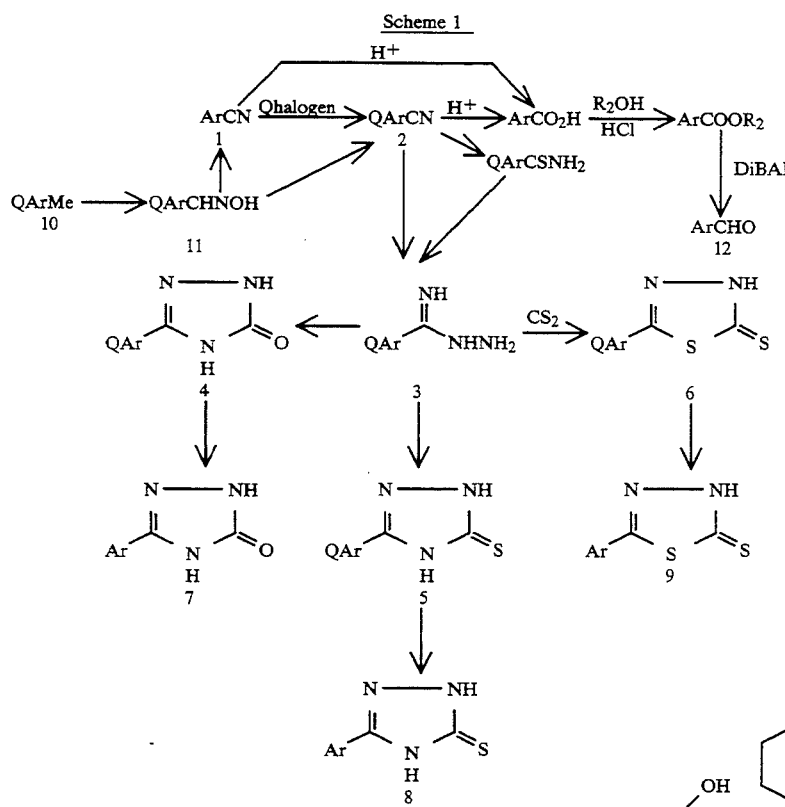

Scheme 1

The procedures which may be used for the preparation of compounds 2 to 4 of Scheme 2 from compound 1 where n=0 or 1 are described below.

Compounds of structure 4 in Scheme 2 are prepared by treating oxime 1 with N-chlorosuccinimide in dimethylformamide (DMF) or dimethylsulfoxide (DMSO), or chlorinated or aromatic or ether solvents at 0° to 60° C. for up to five days to give 2. Compound 3 is prepared by treating 2 with hydrazine and trialkylamine, if only one equivalent of hydrazine is used, in ether solvents or alkanols at 0° to 60° C. for up to 5 days. Treatment of 3 with CS$_2$ in DMF or DMSO or chlorinated or aromatic or ether solvents or alkanols or neat at 0° to 60° C. for up to five days gives 4.

Compounds of structure 4 and 5 in Scheme 3 where n=0 or 1 are prepared by the following procedures.

Compound 3 is prepared from 1 using 2 in DMF or DMSO or chlorinated or ether solvents at 0° to 60° C.

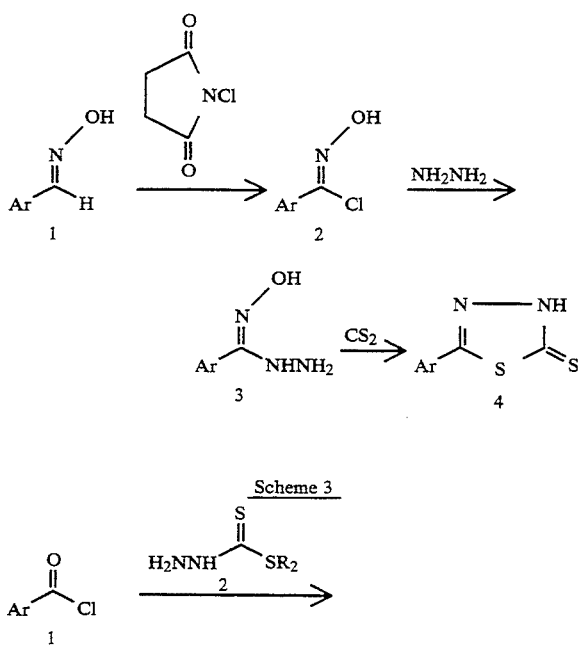

Scheme 3

-continued
Scheme 3

Treatment of 9 with hydrazine in water and alkanols at 0° to 150° C. for up to 5 days gives 11. Compound 10 is prepared from 5 using sodium isocyanate, neutralized with one equivalent of a mineral acid, in alkanols at 0° to 100° C. for up to 5 days.

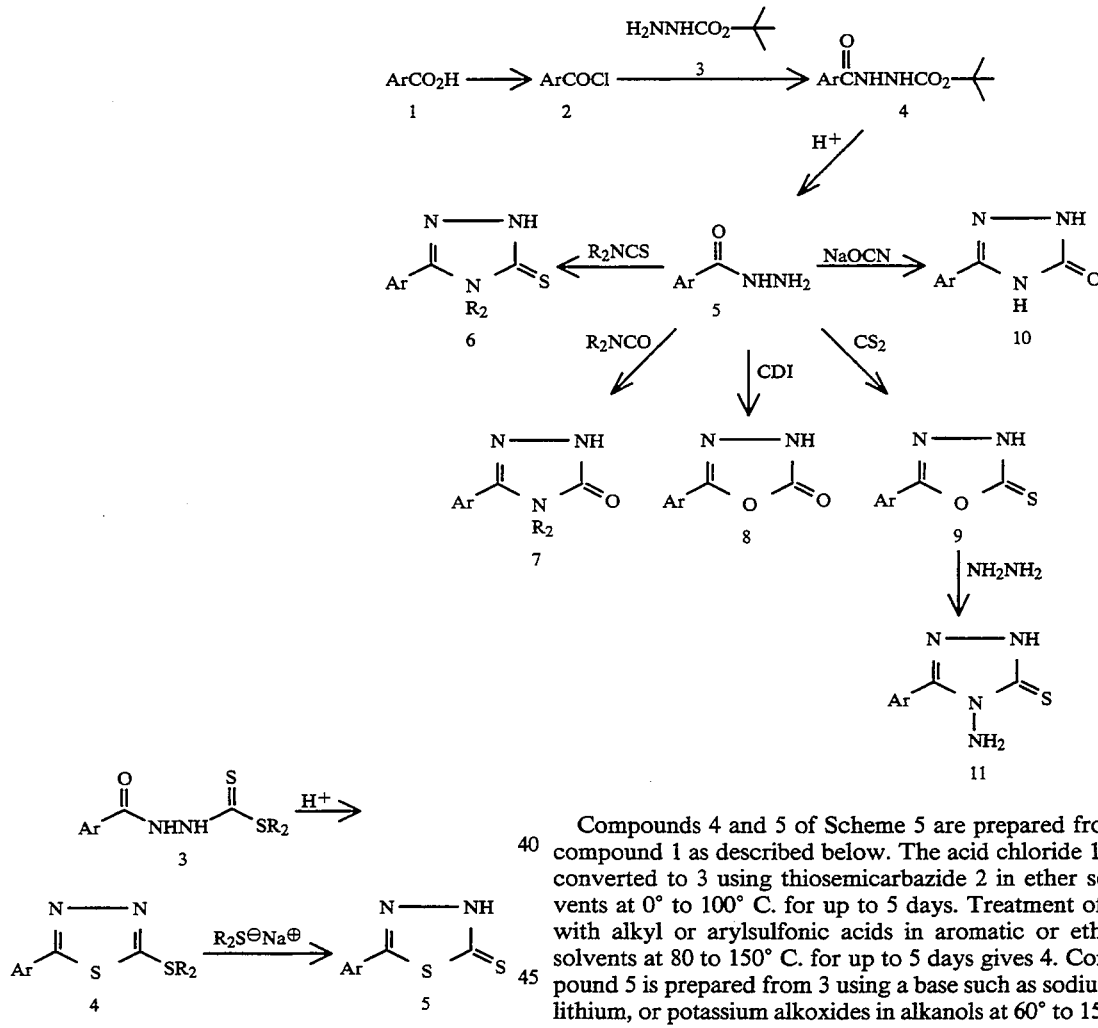

The following procedures for preparing compounds 6 to 11 of Scheme 4 from compound 1 of Scheme 4 where n=0 or 1 are described below. Conversion of 1 to 2 is effected using thionyl chloride or oxalyl chloride and a catalytic amount of DMF in chlorinated or ether solvents at 0° to 100° C. for up to 5 days. Compound 4 is prepared from 2 using 3 in chlorinated, aromatic or ether solvents at 0° to 120° C. for up to 5 days. Treatment of 4 with mineral acids in water and ether solvents or alkanols gives hydrazide 5. Compound 6 is prepared from 5 using alkylisothiocyanates in ether solvents or alkanols at 0° to 100° C. for up to 5 days followed by aqueous NaOH and refluxing the reaction mixture.

Compound 7 is prepared by reacting 5 with alkylisocyanate as described for the preparation of 6. Treatment of 5 with 1,1-carbonyldiimidazole or phosgene or diphosgene or triphosgene in chlorinated or ether solvents in the presence of trialkylamines at 0° to 100° C. for up to 5 days gives 8. Treatment of 5 with $CS_2$ in the presence of one equivalent of KOH in alkanols at 0° to 150° C. gives oxadiazolethione 9.

Compounds 4 and 5 of Scheme 5 are prepared from compound 1 as described below. The acid chloride 1 is converted to 3 using thiosemicarbazide 2 in ether solvents at 0° to 100° C. for up to 5 days. Treatment of 3 with alkyl or arylsulfonic acids in aromatic or ether solvents at 80 to 150° C. for up to 5 days gives 4. Compound 5 is prepared from 3 using a base such as sodium, lithium, or potassium alkoxides in alkanols at 60° to 150° C. for up to 5 days.

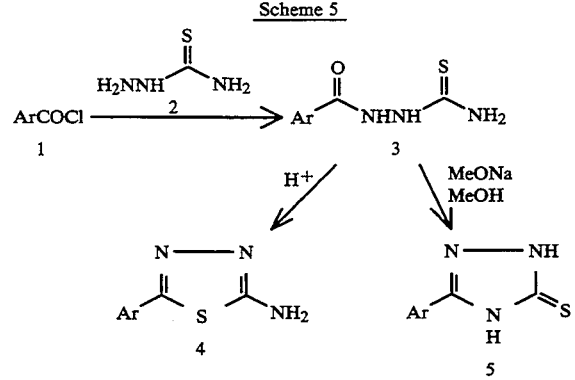

The methods for the preparation of compounds 6–13 in Scheme 6 where $X_1$ is O, S or $NR_1$ and $R_6$ is $CH_2Br$, $CH_2Cl$ or $CH_2NO_2$, and $R_7$ is lower alkyl, phenyl, or $CF_3$, and $R_8$ is $SO_2R_2$, CN or $SO_2$aryl, and $R_9$ is Cl, SR$_2$, SOR$_2$, SO$_2$R$_2$, OR$_2$ or Oaryl are described below. The conversion of 1 where n=0 or 1 to 8, 10, and 13 is effected using 3, 4, and 5, respectively, in solvents such as tetrahydrofuran, diethylether, diisopropyl ether, t-butylmethylether, dioxane, benzene, toluene, acetonitrile, DMF or DMSO at 0° to 150° C. for up to 5 days. Treatment of 1 with 1,1-carbonyldiimidazole, phosgene, diphosgene, or triphosgene in the presence of trialkylamine in aromatic or ether solvents gives 6. Compound 11 is prepared from 10 where X$_1$ is O, S or NR$_2$ and n=0 using lithium, sodium or potassium amide 14 in ether solvents. The conversion of 8 to 9 and 11 to 12 is effected using P$_2$S$_5$ or Lawesson's reagent in ether solvents at 20° to 150° C. for up to 5 days.

Compound 7 is prepared from 1 using trialkyl-orthoesters 2 neat or in alkanols, aromatic or ether solvents in the presence of a catalytic amount of acid such as aryl or alkyl sulfonic acid or mineral acids.

Scheme 6

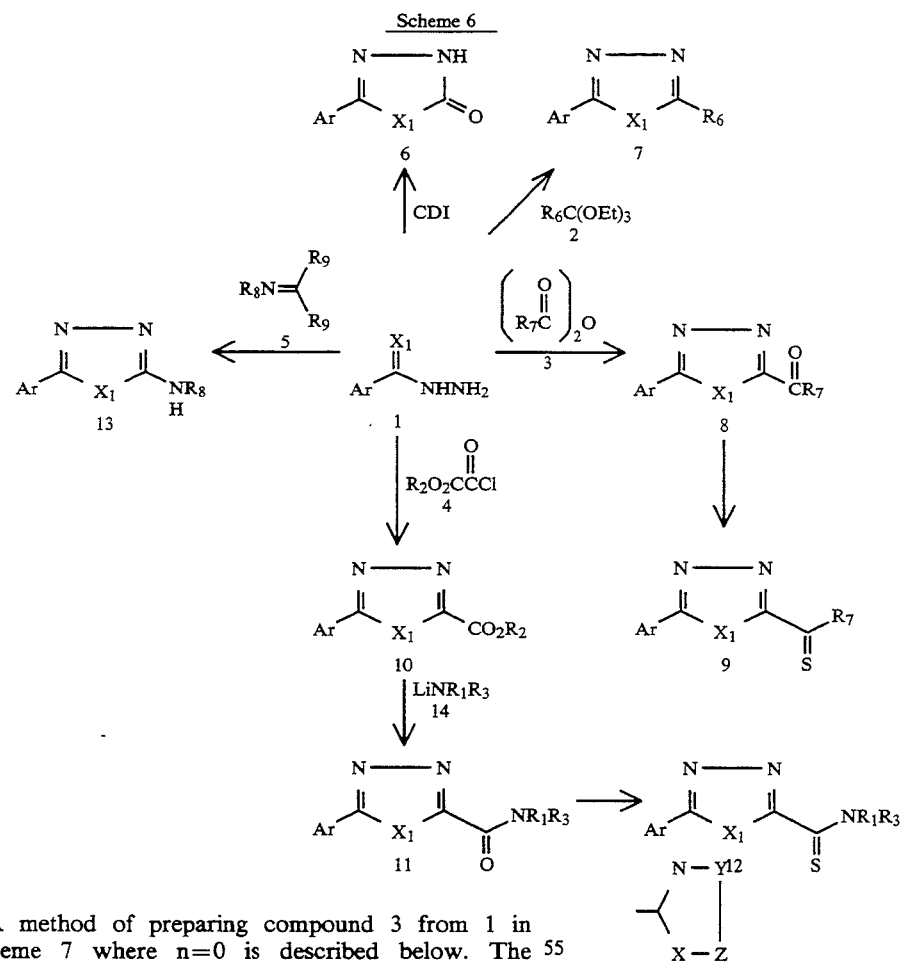

A method of preparing compound 3 from 1 in Scheme 7 where n=0 is described below. The aminoguanidine HCl, H$_2$SO$_4$ or HNO$_3$ salt is neutralized with a sodium, lithium or potassium alkoxide in an alkanol or ether solvent and then treated with 1. The reaction is run at 20° to 150° C. for up to 5 days to give 2. Deprotection of 2 using the above described conditions gives 3.

Scheme 7

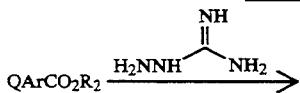

-continued
Scheme 7

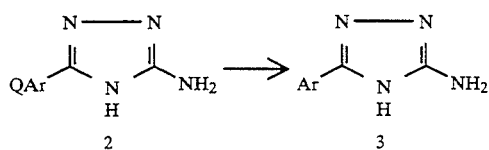

The preparation of substituted 1,2,4-oxadiazoles is well known in the art (see, for example, L. B. Clapp, *Advances in Heterocyclic Chem.*, 20, 65 (1976)).

For a compound of Formula I, wherein n is zero and W is wherein X is O, Z is N, and Y is C—NH$_2$ the procedure of K. R. Huffman and F. C. Schaefer, *J. Org. Chem.*, 28, 1812 (1963), beginning with a suitable imino ester, may be used. Other functional groups, instead of amino, are prepared by the procedures cited below.

| Y | |
|---|---|
| C—OH | F. Eloy, A. Deryckere and A. van Overstraeten, Bull. Soc. Chim. Belges, 78, 47 (1969); and O. Tsuge, S. Urano, and K. Oe, J. Org. Chem., 45, 5130 (1980). |
| C-Halogen | F. Eloy, cited above; and G. R. Humphreys |

| | -continued |
|---|---|
| | and S. H. B. Wright, J. Heterocyclic Chem., 26, 23 (1989). |
| C—SH | D. S. Tarbell and D. K. Fukushima, Organic Syntheses, 27, 81 (1947). |
| C—SR$_2$ | B. W. Nash, R. A. Newberry, R. Pickles, and W. K. Warburton, J. Chem. Soc.(c), 2794 (1969). |

For a compound of Formula I, wherein n is zero and W is

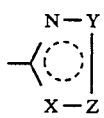

wherein X is N, Z is O, and Y is C—NH$_2$. The procedure of F. Eloy and R. Lenaers, Helv. Chim. Acta, 49, 1430 (1966), involving the reaction of guanidine with a suitable carboxyimidoyl halide may be used. Other functional groups, instead of amino, are prepared by the procedures cited below.

| Y | |
|---|---|
| C—OH | A. R. Katritzky, B. Wallis, R. T. C. Brownlee, and R. D. Topson, Tetrahedron, 21, 1681 (1965). |
| C-Halogen | T. Fujita, T. Fuji, and A. Ide, Yakugaku Zasshi, 84, 1061 (1964). |
| C—SH, | M. Selim and M. Selim, Bull. Soc. Chim. Fr., 823 (1969); and R. M. Paton and |
| C—SR$_2$ | D. G. Hamilton, Tetrahedron Letters, 24, 5141 (1983). |

Preparative procedures for substituted 1,2,4-thiadiazoles are also well known (see, for example, F. Kurzer, Advances in Heterocyclic Chem., 32, 285 (1982)).

For a compound of Formula I, wherein n is zero and W is

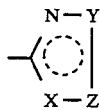

wherein X is N, Z is S, and Y is C-Halogen, the procedure of J. Goerdeler, H. Groschopp, and U. Sommerlad, Chem. Bet., 90, 182 (1957), consisting of condensing perchloromethylmercaptan with a suitable amidine, may be used. The resulting 5-halogen-substituted thiadiazole is then treated with a variety of well-known reagents to prepare analogs in which Y is C—OH, C—SR$_1$, or C—NHR$_1$, wherein R$_1$ is as defined above.

A related synthetic procedure for compounds wherein Y is C—NH$_2$ is that of J. Goerdeler, K. Werebet, and G. Worsch, Chem. Ber., 87, 57 (1954).

For a compound of Formula I, wherein n is zero and W is

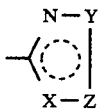

wherein X is S, Z is N, and Y is C—NH$_2$ the procedure of C. G. Newton, W. D. Ollis, and D. E. Wright, J. Chem. Soc. Perk. Trans. I, 75 (1984), or B. Junge, German Patent 2,402,228 (1974), employing substituted thioamides as starting materials, may be used.

When Y is C—OH, the procedure of O. Tsuge, et al, previously cited, or that of J. Perronnet, L. Taliani, and A. Teche, U.S. Pat. No. 4,067,720 (1978), may be advantageously employed.

Additional thiadiazole analogs are prepared by diazotization of amines and other standard transformations.

Schemes 8–13 outline the functional group transformation which may be performed on Y in compounds of formula I.

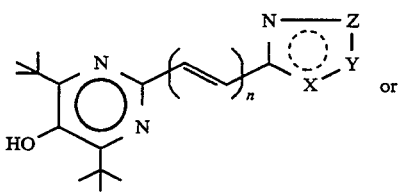

or

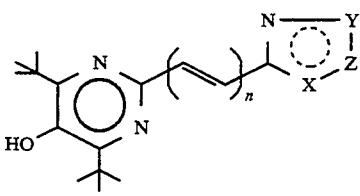

wherein n, Y, X, and Z are described above.

Under certain circumstances discussed below the phenolic OH of 1 may be protected as described above to give

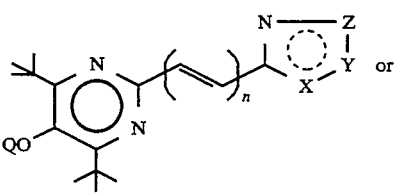

or

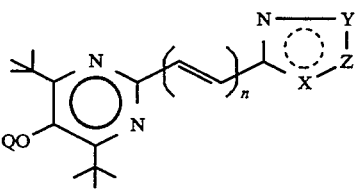

wherein Q is a protecting group as described above, and n, X, Y, and Z are described above.

Scheme 8 shows methods for the conversion of compounds of type I wherein Y is C—OH (1) to compounds of type I wherein Y is C—OAlkyl (2) by treatment of 1 with an alkyl halide in the presence of a base such as NaH, NaOH, KOH, KH, LiOH, t-BuOH or triethylamine.

Treatment of 1 with PCl$_5$, PCl$_3$, or POCl$_3$ in benzene, toluene, chloroform or methylene chloride gives a compound of type 3. Treatment of 4 under standard Sandmeyer reaction conditions also yields 3.

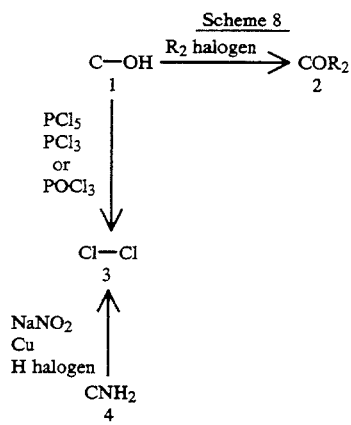

Scheme 9 shows processes for conversion of compounds of type I wherein Y is C—SH (1) to compounds 2, 3, 4, 5, 6, and 7.

Treatment of 1 with bases such as KH, NaH, or t-BuOK in the presence of an omega-halocarboxylic lower alkylester in an aprotic solvent such as diethylether, tetrahydrofuran or dimethylformamide, gives 2. Hydrolysis of 2 under standard basic conditions give the corresponding acid 4.

Treatment of 1 with alkyl halides under the conditions described above gives 3.

Treatment of 3 with excess oxidizing agents such as KMnO$_4$, H$_2$O$_2$ in acetic acid, or m-chloroperbenzoic acid (MCPBA) in chloroform or methylene chloride gives sulfone 5. Treatment of 3 with one equivalent of the above oxidizing agent gives sulfoxide 6.

Treatment of 1 with an oxidizing agent such as chlorine in acetic acid or sodium hyperchlorite, followed by an amine gives a sulfonamide of type 7.

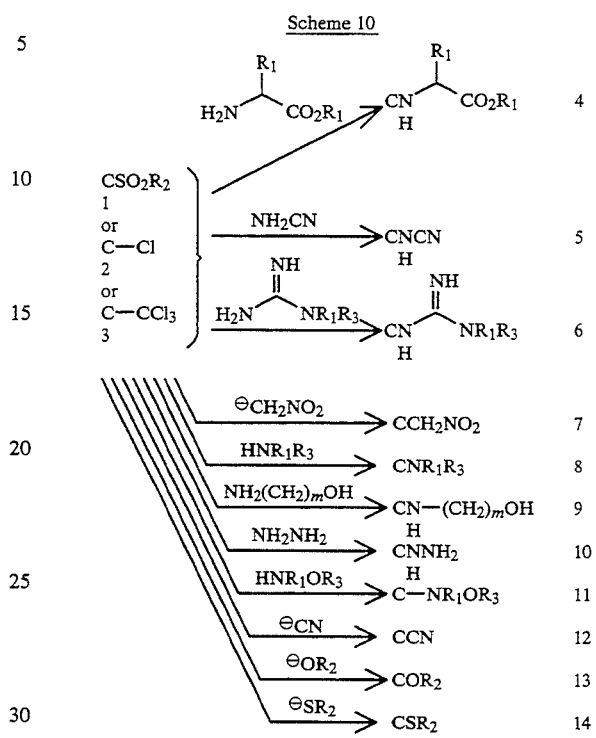

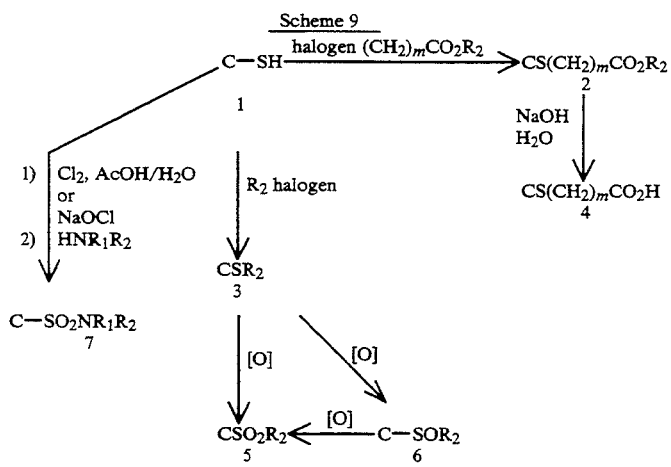

Scheme 10 shows the conversion of compounds of type I wherein Y is C—SO$_2$R$_2$ (1), C—Cl (2) or C—CCl$_3$ (3) to compounds 4, 5, 6, 7, 8, 9, 10, 11, 12, 13, and 14 on treatment with the nucleophiles listed in Scheme 10.

Compounds 7, 12, 13, and 14 are prepared by treating 1, 2, or 3 with the sodium or potassium salt of the respective anion in a solvent such as DMF.

Compounds 4, 5, 6, 8, 9, 10, and 11 are prepared by treating 1, 2, or 3 with the respective nucleophile in a solvent such as ethanol, isopropanol, tertiary butanol, or DMF/water. Triethylamine or sodium tertiary butoxide are added in cases in which neutralization of an acid is required.

In Scheme 11 where R$_5$ is OR$_2$, R$_1$ or aryl and R$_{10}$ is Cl, OR$_2$, SR$_2$, treatment of compounds of type I wherein Y is C—NH$_2$ with isocyanates or isothiocyanates in hexane, benzene or toluene gives compounds 2, 3,4, and 5. Treatment of 1 with sodium nitrite in sulfuric acid, followed by hydrolysis of the diazonium salt gives 7. Alkylation, acylation, or sulfonylation of 1 with various electrophiles gives compounds 6, 8, 12, and 13. Amine 8 can be further treated with other electrophiles to yield 9, 10, and 11. Amides 9 and 12 are converted to the corresponding thioanlides 10 and 13 with treatment with P$_2$S$_5$ or Lawesson's reagent.

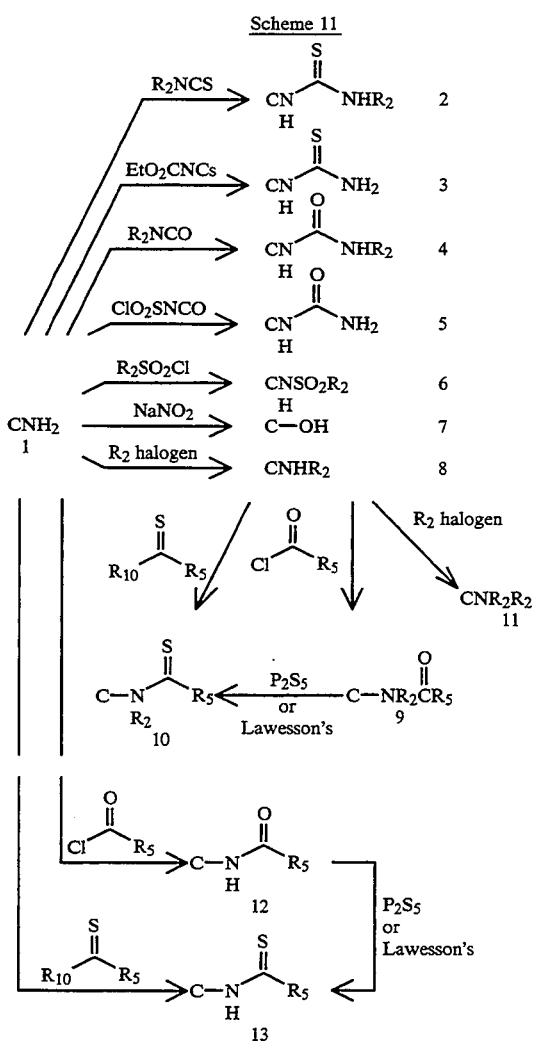

In Scheme 12, treatment of compounds of type I wherein Y is C—CH$_2$Cl with various nucleophiles in dimethylsulfoxide or dimethylformamide gives 2, 3, and 4. Treatment of 4 with excess oxidizing agent such as KMnO$_4$, H$_2$O$_2$ in acetic acid, or M-chloroperbenzoic acid (MCPBA) in chloroform or methylene chloride gives sulfone 5.

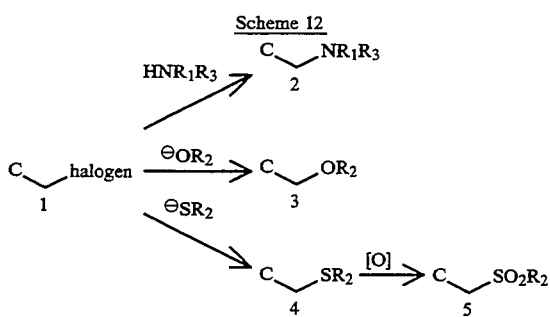

Methods for the preparation of 5, 6, and 7 in Scheme 13 are described below. Compound 1 may be converted to 5, 6, or 7 using 2, 3 or 4, respectively, in aromatic, chlorinated or ether solvents at 0° to 200° C. The base such as sodium methoxide, potassium butoxide or triethylamine may be needed to catalyze the reaction or to neutralize acid that may be produced. This step is followed by treatment of the reaction with HNR$_1$R$_3$ to give 5, 6, or 7, respectively.

Treatment of 8 in Scheme 13 with R$_2$halogen in ether solvents in the presence of a base such as sodium methoxide, potassium t-butoxide or triethylamine at 0° to 150° C. gives 9. Compounds 5, 6 or 7 may be prepared from 9 using 10, 11, or 12, respectively, in aromatic or ether solvents at 0° to 150° C. The anion of compound 10 may be generated using bases such as triethylamine, potassium t-butoxide, or sodium hydride. The reactions using 11 and 12 could employ a base such as potassium, sodium, t-butoxide, triethylamine. The phenolic OH of 1, 8, or 9 may be protected with Q as described above.

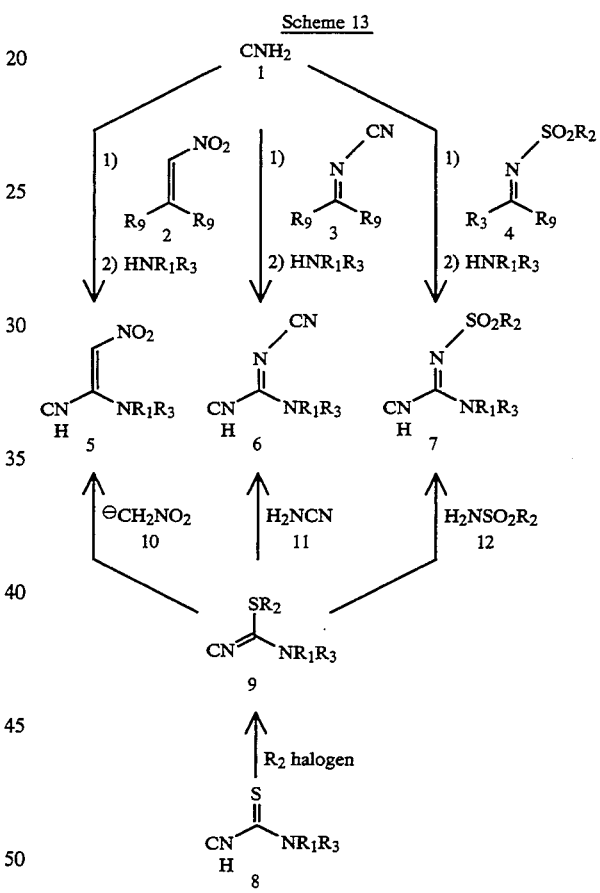

One of skill in the art would recognize variations in the sequence and would recognize variations in the appropriate reaction conditions from the analogous reactions shown or otherwise known which may be appropriately used in the processes above to make the compounds of the Formula I herein. For example, variations in the protecting groups are well known to an ordinary skilled artisan. Further, starting materials are known or can be prepared by known methods.

The products of the reactions described herein are isolated by conventional means such as extraction, distillation, chromatography, and the like.

The invention is further elaborated by the representative examples as follows. Such examples are not meant to be limiting.

EXAMPLE 1

5-[4,6-Bis(1,1-dimethylethyl)-5-hydroxy-2-pyrimidinyl]-1,3,4-thiadiazole-2(3H)-thione 5-[4,6-bis (1,1-dimethylethyl)-5-[(2-methoxyethoxy)methoxy]-2-pyrimidinyl]-1,3,4-thiadiazole-2(3H)-thione (0.18 g, 0.41 mmoles) is dissolved in 10 mL of dichloromethane. Zinc (II) bromide (0.98 g, 4.4 mmol) is added and the reaction mixture is stirred at room temperature under argon for 14 hours.

Zinc (II) bromide (0.5 g, 2.1 mmoles) is added and the reaction mixture is stirred at room temperature for 4 hours, at which time another 0.5 g of zinc (II) bromide is added. After being stirred for an additional 4 hours at room temperature, the reaction is quenched with 20 mL of water. The layers are separated, and the aqueous phase is extracted with dichloromethane (3×20 mL). The combined dichloromethane extracts are washed with 50 mL of brine and dried over magnesium sulfate. The solvent is evaporated, and the remaining oil is purified by flash chromatography (silica, 50% ethyl acetate/hexane). Yield of 5-[4,6-bis (1,1-dimethylethyl) -5-hydroxy-2-pyrimidinyl]-1,3,4-thiadiazole-2(3H)-thione=0.03 g, mp 225°–230° C.

EXAMPLE 2

4,6-Bis(1,1-dimethylethyl)-5-[(2-methoxyethoxy)methoxy]-2-pyrimidinecarbonitrile Dimethylformamide (0.05 g, 0.6 mmoles) is cooled to 0° C. in 10 mL of acetonitrile under argon. Oxalyl chloride (0.1 g, 0.9 mmoles) is added and the reaction mixture is stirred at 0° C. for 10 minutes. 4,6-Bis(1,1-dimethylethyl)-5-[(2-methoxyethoxy)-methoxy] -2-pyrimidinecarboxaldehyde oxime (0.2 g, 0.6 mmoles) is dissolved in 10 mL of acetonitrile and cooled to 0° C. The vilsmier reagent prepared above is added to the pyrimidine solution at 0° C. After 3 hours at 0° C., the reaction is quenched by the addition of 10 mL of saturated sodium bicarbonate and extracted with ether (3×10 mL). The organic extract is washed with 50 mL of brine and dried over magnesium sulfate. Evaporation of the solvent gives a red oil which is purified by flash chromatography (silica, 10% ether/chloroform) to give 4,6-bis (1,1-dimethylethyl)-5-[(2-methoxyethoxy) methoxy]-2-pyrimidinecarbonitrile (43 mg, 22%) as an oil.

$H^1$-NMR (CDCl$_3$) δ5.04 (s, 2H, O—CH$_2$—O) , 3.95 (m, 2H) , 3.62 (m, 2H) , 3.41 (s, 3H, OCH$_3$) , 1.44 (s, 18H, C(CH$_3$)$_3$).

EXAMPLE 3

4,6-Bis(1,1-dimethylethyl)-5-[(2-methoxyethoxy) , methoxy]-2-pyrimidinecarboxaldehyde oxime Sodium metal (0.28 g, 12.6 mmoles) is dissolved in 50 mL of freshly distilled ammonia at reflux under argon. The reaction mixture is stirred at reflux until the solution turns light gray. 4,6-Bis(1,1-dimethylethyl)-5-[(2-methoxyethoxy)-methoxy]-2-methyl-pyrimidine (3.0 g, 9.7 mmoles) is dissolved in 20 mL of tetrahydrofuran and added to the reaction. After 10 minutes, isoamyl nitrite (2.3 g, 19.3 mmoles) is added, and the reaction mixture is stirred at reflux for 2 hours. It is quenched by the addition of ammonium chloride (1.0 g, 18.7 mmoles) and the ammonia is allowed to evaporate at room temperature. The remaining oil is partitioned between 50 mL of ethyl acetate and 50 mL of water. The organic layer is washed with water (3×50 mL) and brine (50 mL), dried over magnesium sulfate, and the solvent is evaporated. The crude product is adsorbed onto a silica gel plug which is eluted with 300 mL of 5% ether in chloroform, followed by 300 mL of ether. Evaporation of the ether eluant gives 4,6-bis (1,1-dimethylethyl)-5-[(2-methoxyethoxy)methoxy]-2-pyrimidine-carboxaldehyde oxime (0.7 g, 21%) , mp 90°–97° C.

$H^1$-NMR (CDCl$_3$) δ10.40 (s, 1H=NOH) , 8.17 (s, 1H, HON=CH<bs>—__—) , 5.00 (s, 2H, O—CH$_2$—O) , 3.97 (m, 2H) , 3.64 (m, 2H) , 3.42 (s, 1H, OCH$_3$) , 1.45 (s, 18H, C(CH$_3$)$_3$). $C^{13}$-NMR (CDCl$_3$) δ170, 155, 148, 147, 102, 72, 70, 60, 39, 30.

EXAMPLE 4

5-[4,6-Bis(1,1-dimethylethyl)-5-[(2-methoxyethoxy)-methoxy]-2-pyrimidinyl]-1,3,4-thiadiazole-2 (3H)thione 4,6-Bis(1,1-dimethylethyl)-5-[(2-methoxyethoxy)-methoxy]-2-pyrimidinecarbothioamide (0.22 g, 0.6 mmoles) is dissolved in 5 mL of methanol and added dropwise to 10 mL of 5% hydrazine in methanol at 0° C.. The reaction mixture is stirred at 0° C. for 1 hour, and then diluted with 20 mL of water. The methanol is evaporated under reduced pressure, and the organics are extracted into 50 mL of ethyl acetate. The ethyl acetate extract is washed with brine (4×50 mL) and dried over magnesium sulfate. The solvent is evaporated and the crude amidrazone is dissolved in 10 mL of methanol. Carbon disulfide (0.23 g, 3.1 moles) is added at room temperature. After 10 minutes, the methanol is evaporated and the remaining oil is adsorbed onto a silica gel pad. The pad is eluted with 50% ether/hexane. Evaporation of the eluant gives 0.18 g (73%) of 5-[4,6-bis (1,1-dimethylethyl) -5-[(2-methoxyethoxy) methoxy]-2-pyrimidinyl]-1,3,4-thiadiazole-2 (3H)-thione as an oil. This product is used without further purification in the deprotection reaction.

EXAMPLE 5

4,6-Bis(1,1-dimethylethyl)-5-[(2-methoxyethoxy)-methoxy]-2-pyrimidinecarbothioamide 4,6-Bis(1,1-dimethylethyl)-5-[(2-methoxyethoxy) methoxy]-2-pyrimidinecarbonitrile (0.9 g, 2.8 mmoles) is dissolved in 5 mL of pyridine with triethylamine (0.3 g, 3.1 mmoles). Hydrogen sulfide is bubbled into the reaction mixture at room temperature for 2 hours. The reaction mixture is stirred at room temperature for 12 hours, at which time the solvents are evaporated under reduced pressure. The remaining oil is taken up in 100 mL of ether and washed with water (3×50 mL) followed by 50 mL of brine. The organic layer is dried over magnesium sulfate and evaporated to give a crude oil. Flash chromatography (silica, 10% ether/chloroform) gives 4,6-bis (1,1-dimethylethyl)-5-[(2-methoxyethoxy) methoxy]-2-pyrimidinecarbothioamide as an oil. Yield=0.7 g (70 %).

$H^1$-NMR (CDCl$_3$) δ9.14 (br, 1H) , 7.72 (br, 1H) , 5.02 (s, 2H, O—CH$_2$—O) , 3.96 (m, 2H) , 3.64 (m, 2H) , 3.41 (s, 3H, O—CH$_3$) , 1.48 (s, 18H, C (CH$_3$)$_3$).

The following examples (Examples 6–8) show the overall preparation of 4,6-bis (1,1-dimethylethyl)-5-[ (2-methoxyethoxy) methoxy]-2-methylpyrimidine for use in Example 3.

EXAMPLE 6

1-[4-(1,1-Dimethylethyl)-2-methyl-5-oxazolyl]-2,2-dimethyl-1-propanone

A solution of 4-(acetyloxy)-2,2, 6, 6-tetramethyl 3,5-heptanedione (22 g, 0.09 mol) in acetic acid (100 mL) is treated with ammonium acetate (44 g). The reaction mixture is heated at reflux overnight. The reaction mixture is diluted with water and neutralized (to pH 5) by the addition of aqueous sodium hydroxide. The product is extracted into ethyl acetate (3×150 mL) and the combined organic layers are washed with 0.1 N NaOH, water, and then brine. The organic layer is dried and evaporated. The residue is taken up in hexane (50 mL) and applied to a pad of silica gel (500 g). The silica pad is eluted with hexane (100 mL). Then the product is eluted from the silica with hexane/ethyl acetate (4:1) to give 18.6 g (91%) of 1-[4-(1,1-dimethylethyl) -2-methyl-5-oxazolyl]-2,2-dimethyl-1-propanone as an oil.

$^1$H-NMR (CDCl$_3$) δ2.60 (s, 3H, 2-Me) , 1.35 (s, 9H, tbu) , 1.31 (s, 9H, tbu). $^{13}$C-NMR (CDCl$_3$) δ195.8, 159.3, 157.6, 143.6, 44.2, 32.7, 28.4, 26.6.

EXAMPLE 7

4,6-Bis(1,1-dimethylethyl)-5-hydroxy-2-methyl pyrimidine

A mixture of 1-[4-(1,1-dimethylethyl-2-methyl-5-oxazolyl]-2,2-dimethyl-l-propanone (8.5 g, 38 mmol) and concentrated ammonium hydroxide (100 mL) is heated at 180° C. for 36 hours in a steel bomb. The reaction mixture is cooled and the excess ammonia is evaporated on the rotovap. The pH of the resulting mixture is adjusted to pH 6 with concentrated HCl with ice bath cooling. The product is extracted into ether (3×250 mL) and the organic layer is dried (MgSO$_4$) and evaporated. The residue is purified by flash chromatography (silica, 7% EtOAc/hexane) to give pure 4,6-bis (1,1-dimethylethyl) -5-hydroxy-2-methylpyrimidine (6.35 g, 75%) as a partial hydrate; mp 62°–65° C.

$^1$H-NMR (d$_6$-DMSO) δ7.76 (br, 1H, OH) , 2.45 (s, 3H, CH$_3$) , 1.36 (s, 18H, t-bu). $^{13}$C-NMR (CDCl$_3$) δ161.2, 157.5, 145.1,37.0, 28.7, 25.4.

The compound is further characterized by conversion to its acetyl derivative, mp 45°–47° C.

EXAMPLE 8

4,6-Bis(1,1-dimethylethyl)-5-[(2-methoxyethoxy)-methoxy]-2-methylpyrimidine 4,6-Bis(1,1-dimethylethyl)-5-hydroxy-2-methyl pyrimidine (9.8 g, 44.1 mmoles) is dissolved in 100 mL of tetrahydrofuran and added dropwise to a suspension of sodium hydride (1.2 g, 48.5 mmoles) in THF (50 mL) at 0° C. The reaction mixture is warmed to room temperature over 15 minutes. 2-Methoxy-ethoxymethyl chloride (7.1 g, 57.3 mmoles) is added to the reaction mixture at room temperature. After being stirred at room temperature for 4 hours, the reaction is quenched by the addition of saturated ammonium chloride and the tetrahydrofuran is evaporated. The organics are extracted into 300 mL of ether. The ether is washed with 100 mL of brine and dried over magnesium sulfate. Evaporation of the solvent gives the crude product which is purified by flash chromatography (silica, 10% ether/hexane). Yield of 4,6-bis (1,1-dimethylethyl)-5-[(2-methoxyethoxy) methoxy]-2-methylpyrimidine=11.3 g (82%) as a clear oil.

$^1$H-NMR-(CDCl$_3$) δ4.96 (s, 2H, O—CH$_2$—O), 3.93 (m, 2H), 3.60 (m, 2H), 3.39 (s, 3H, O—CH$_3$), 2.54 (s, 3H, CH$_3$), 1.40 (s, 18H, C (CH$_3$)$_3$). C$^{13}$-NMR (CDCl$_3$) δ169.2, 159.8, 145.7, 99.9, 71.5, 69.4, 58.9, 38.2, 30.0, 25.2.

EXAMPLE 9

4,6-Bis(1,1-dimethylethyl)-5-[(2-methoxyethoxy)-methoxy]-2-pyrimidine carboxylic acid hydrazide 4,6-Bis(1,1-dimethylethyl)-5-[(2-methoxyethoxy) methoxy]-2-pyrimidine carboxylic acid methyl ester (5.0 g, 14. 0 moles) is dissolved in 50 mL of MeOH at room temperature. Hydrazine (4.5 g, 14.0 mmoles) is added and the reaction mixture is stirred at room temperature for 3 hours. It is diluted with 100 mL of water and the methanol is evaporated under reduced pressure. The organic material is extracted into EtOAc (4×100 mL). The EtOAc extract is washed with brine (2×100 mL) and dried over MgSO$_4$. Evaporation of solvent on the rotovap gives 4.8 g of a clear oil which solidifies on standing overnight. Yield of 4,6-bis(1,1-dimethylethyl)-5-[(2-methoxyethoxy) methoxy]-2-pyrimidine carboxylic acid hydrazide=4.8 g (96%). An aliquot is triturated with hexane. The solid remaining is dried under vacuum over P$_2$O$_5$ at 110° C., mp 67°–69° C.

Analysis for C$_{17}$H$_{30}$N$_4$O$_4$: Calcd.: C, 57.30; H, 8.49; N, 16.21. Found: C, 57.61; H, 8.53; N, 15.81.

EXAMPLE 10

5-[4,6-Bis(1,1-dimethylethyl)-5-hydroxy-2-pyrimidinyl]-1,3,4-oxadiazole-2(3H)-one 4,6-Bis(1,1-dimethylethyl)-5-[(2-methoxyethoxy) methoxy]-2-pyrimidine carboxylic acid hydrazide (1.0 g, 2.8 mmoles), carbonyl diimidazole (0.7 g, 4.2 mmoles), and triethylamine (0.6 g, 5.9 mmoles) are combined in 20 mL of THF and the reaction mixture is stirred at room temperature under argon for 64 hours. The reaction is quenched with 50 mL of 10% HOAc/H$_2$O. The organics are extracted into ether (3×30 mL) and washed with 50 nil of brine. The solvent is evaporated and the residue is taken up in 20 mL of acetic acid. The reaction mixture is warmed to reflux for 18 hours. It is cooled to room temperature and diluted with 150 mL of H$_2$O. The organics are extracted into EtOAc (3×100 mL) and washed with H$_2$O (3×100 mL) followed by brine (3×100 mL). The solvent is evaporated, and the remaining oil is purified by flash chromatography (50% EtOAc|Hexane). Yield of 5-[4,6-bis (1,1-dimethylethyl)-5-hydroxy-2-pyrimidinyl]-1,3,4-oxadiazole-2 (3H)-one=0.11 g (13%), mp 230°–232° C.

Analysis for C$_{14}$H$_{20}$N$_4$O$_3$: Calcd.: C, 57.52; H, 6.90; N, 19.16. Found: C, 57.73; H, 6.92; N, 19.02.

EXAMPLE 11

5-[4,6-Bis(1,1-dimethylethyl)-5-hydroxy-2-pyrimidinyl]-1,3,4-2H-oxadiazole 4,6-Bis(1,1-dimethylethyl)-5-[(2-methoxyethoxy)-methoxy]-2-pyrimidine carboxylic acid hydrazide (0.5 g, 1.4 mmoles) is dissolved in 10 mL of triethylorthoformate along with a catalytic amount of p-toluene sulfonic acid. The reaction mixture is stirred at room temperature for 24 hours. The reaction is quenched with 50 mL of 10% HOAc/H$_2$O. The organics are extracted into EtOAc (3×50 mL) and washed with brine (3×50 mL). The solvent is evaporated and the residue is dissolved in trifluoroacetic acid (TFA) (10 mL). The reaction mixture is stirred at room temperature for 20 minutes and then poured into 50 mL H$_2$O. The organics are extracted into EtOAc (3×50 mL) and washed with H$_{20}$ (3×50 mL) followed by brine (3×50 mL). Drying over MgSO$_4$ and evaporation of solvent gives a red oil. Flash chromatography in 40% EtOAc/hexane gives 78 mg (20%) of 5-[4,6-bis (1,1-dimethylethyl)-5-hydroxy-2-pyrimidinyl]1,3,4-2H-oxadiazole, 165°–169° C.

Analysis for C$_{14}$H$_{20}$N$_4$O$_2$: Calcd.: C, 60.85; H, 7.30; N, 20.27. Found: C, 61.16; H, 7.49; N, 19.88.

EXAMPLE 12

5-[4,6-Bis(1,1-dimethylethyl)-5-hydroxy-2-pyrimidinyl]-1,3,4-oxadiazole-2 (3H)-thione 4,6-Bis(1,1-dimethylethyl)-5-[(2-methoxyethoxy) methoxy]-2-pyrimidine carboxylic acid hydrazide (0.9 g, 2.5 mmoles), KOH (0.16 g, 2.8 mmoles), and carbon disulfide (0.44 g, 5.8 mmoles) are dissolved in 20 mL of MeOH. The reaction mixture is warmed to reflux under argon for 24 hours. It is cooled to room temperature, quenched with 150 mL of 10% HOAc/H$_2$O, and extracted with ether (3×100 mL). The ether extract is washed with brine (3×100 mL) and evaporated. The oil remaining is taken up in 20 mL of TFA and stirred at room temperature for 30 minutes. The TFA is evaporated on the rotovap, and the oil is partitioned between 100 mL of ether and 100 mL of H$_2$O. The pH of the water layer is adjusted to 5 by the addition of saturated sodium bicarbonate. The layers are separated and the organic layer is washed with 50 mL of brine. Drying over MgSO$_4$ and evaporation of solvent gives a yellow oil. Flash chromatography in 50% Et$_2$O/hexane followed by two recrystallizations from Et$_2$O/hexane gives 0.16 g (20%) of 5-[4,6-bis (1,1-dimethylethyl)-5-hydroxy-2-pyrimidinyl]-1,3,4-oxadiazole-2 (3H)-thione, 234°–236° C. dec.

Analysis for C$_{14}$H$_{20}$ON$_4$O$_2$S: Calcd.: C, 54.52; H, 6.54; N, 18.17; S, 10.40. Found: C, 54.46; H, 6.40; N, 18.38; S, 10.53.

EXAMPLE 13

5-[4,6-Bis(1,1-dimethylethyl)-5-hydroxy-2-pyrimidinyl]-2-thiomethoxy-1,3,4-3H-thiadiazole 5-[4,6-Bis(1,1-dimethylethyl)-5-hydroxy-2-pyrimidinyl]-1,3,4-thiadiazole-2 (3H)-thione (0.5 g, 1.5 mmoles), triethylamine (0.17 g, 1.7 mmoles), and methyl iodide (0.22 g, 1.5 mmoles) are stirred in 20 mL of THF at 0° C. for 1.5 hours. The THF is removed under reduced pressure, and the remaining solid is partitioned between 50 mL of ether and 50 mL of water. The layers are separated and the ether layer is washed with 50 mL of brine. Drying over MgSO$_4$ and evaporation of solvent gives a yellow oil. Flash chromatography in 20% EtOAc/hexane gives 230 mg of 5-[4,6-bis (1,1-dimethylethyl)-5-hydroxy-2-pyrimidinyl ]-2-thiomethoxy-1,3,4-3H-thiadiazole.

EXAMPLE 14

Preparation of 4,6-Bis(1,1-dimethylethyl)-5-[(2-methoxyethoxy)-methoxy]-2-pyrimidine carboxylic acid thiomethyl orthoester To a solution of sodium amide (602 mmol) in liquid ammonia is added 4,6-bis-(1,1-dimethylethyl)-5-[(2-methoxyethoxy)-methoxy]-2-methylpyrimidine (53.4 g, 172.0 moles) dissolved in 50 mL of THF.

The reaction mixture is stirred for one half hour and then cooled to −78° C. Dimethyldisulfide (50.2 g, 533.2 mmoles) is added to the reaction mixture over 20 minutes. When addition is complete, the reaction mixture is warmed to reflux for 1 hour.

The reaction is quenched by the slow addition of 27 g of solid NH$_4$Cl and the NH$_3$ is evaporated through a trap containing 500 mL of 10% (W/V) aqueous NaOH. The reaction mixture is partitioned between 200 mL of Et$_2$O and 200 mL of 1.0 N NaOH. The aqueous layer is extracted with Et$_2$O (3×200 mL). The combined organic extracts are washed with 1.0 N NaOH (2×100 mL) and 100 mL of brine. Drying over MgSO$_4$ and evaporation of the solvent gives 80.5 g (100%) of the desired orthoester as an oil.

EXAMPLE 15

Preparation of 4,6-Bis-(1,1-dimethylethyl.)-5-hydroxy-2-pyrimidine carboxylic acid methyl ester HgCl$_2$ (73.05 g, 269.1 mmoles) is added slowly to a solution of 4,6-bis-(1,1-dimethylethyl)-5-[(2-methoxyethoxy) methoxy]-2-pyrimidine carboxylic acid thiomethyl orthoester (80.5 g, 179.4 mmoles) in 400 mL of MeOH at room temperature and the reaction mixture is stirred for 1 additional hour.

The reaction mixture is diluted with 400 mL of CH$_2$Cl$_2$ and stirred for 10 minutes. The precipitate is removed by filtration through celite and the filtrate is concentrated on the rotovap. The residue is taken up in 300 mL of CH$_2$Cl$_2$ and washed with saturated NH$_4$Cl (3×100 mL). Drying over MgSO$_4$ and evaporation of the solvent gives a brown solid. Recrystallization from 200 mL of hexane gives 30.0 g (63%) of the desired ester. MP=131°–133° C.

EXAMPLE 16

Preparation of 4,6-Bis-(1,1-dimethylethyl)-5[(2-methoxyethoxy)methoxy]pyrimidine carboxylic acid methyl ester 4,6-Bis-(1,1-dimethylethyl)-5-[(2-methoxyethoxy) methoxy]-2-pyrimidine carboxylic acid thiomethyl orthoester (41.8 g, 93.1 mmoles) is dissolved in 400 mL of 5% H$_{20}$/MeOH, and cooled in a dry ice/acetone bath to −40° C. H$_2$O (32.3 g, 149.0 mmoles) and HgCl$_2$ (101.2 g, 372.6 mmoles) are added to the reaction mixture, and the dry ice/acetone bath is removed. The solution is allowed to warm to room temperature for 1 hour. The reaction mixture is diluted with 500 mL of CH$_2$Cl$_2$ and stirred for 5 minutes. The solid is removed by filtration, and the filtrate is concentrated on the rotovap. The residue is taken up in 500 mL of CH$_2$Cl$_2$ and washed with saturated NH$_4$Cl (2×200 mL) followed by 100 mL of brine. Drying over MgSO$_4$ and evaporation of solvent gives a yellow oil. Flash chromatography in Et$_2$O gives 23.9 g (79%) of the desired methyl ester.

EXAMPLE 17

Preparation of 4,6-Bis-(1,1-dimethylethyl)-5-[(2-methoxyethoxy)methoxy]-2-pyrimidine carboxaldehyde A solution of di-isobutylaluminum hydride (22.6 mL, 1.5 M in toluene) is added slowly (over a period of 30 minutes) to a solution of 4,6-bis-(1,1-dimethylethyl)-5-[(2-methoxyethoxy) methoxy]-2-pyrimidine carboxylic acid methyl ester (10.0 g, 28.2 mmoles) in 100 mL of toluene at −78° C. under an argon atmosphere.

After 3 hours, additional di-isobutyl aluminum hydride (6.2 mL, 1.5 M, in toluene) is added to this reaction mixture at −78° C., and the mixture is stirred at −78° C. for an additional 2 hours. The reaction is quenched with 100 mL of 10% HOAc/H$_2$O, and the mixture is warmed to room temperature. The organics are extracted into Et$_2$O (3×100 mL). The combined organic layers are washed with 100 mL of 10% HOAc/H$_2$O followed by 100 mL of brine. Drying over MgSO$_4$ followed by evaporation of solvent gives 8.9 g (97%) of the desired aldehyde as an oil.

EXAMPLE 18

4,6-Bis(1,1-dimethylethyl)-5-hydroxy-2-pyrimidine carboxaldehyde

Trifluoroacetic acid (1.05 g, 9.2 mmol) is added to a solution of 4,6-bis (1,1-dimethylethyl)-5-[(2-methoxyethoxy) methoxy]-2-pyrimidine carboxaldehyde (1. 0 g, 3.1 mmol) in methylene chloride and the reaction mixture is stirred at room temperature for 5 hours. The reaction mixture is neutralized by the addition of saturated aqueous NaHCO$_3$ and the layers separated. The organic layer is washed with brine (50 mL), dried over MgSO$_4$, and evaporated. Recrystallization of the residue from hexane gives pure 4,6-bis (1,1-dimethylethyl)-5-hydroxy-2-pyrimidine carboxaldehyde (0.24 g, 33%); mp 187°–189° C.

EXAMPLE 19

4,6-Bis.(1,1-dimethylethyl)-5-hydroxy-2-pyrimidine carbonitrile

According to the procedure of Example 18, 4,6-bis (1,1-dimethylethyl)-5-[(2-methoxyethoxy)-methoxy]-2-pyrimidine carbonitrile (9.1 g, 28.3 mmol) is treated with trifluoroacetic acid to give 4,6-bis (1,1-dimethylethyl)-5-hydroxy-2-pyrimidine carbonitrile (4.5 g, 68%); mp 203°–205° C.

EXAMPLE 20

4,6-Bis(1,1-dimethylethyl)-5-hydroxy-2-pyrimidine carboxaldehyde oxime

A solution of 4,6-bis (1,1-dimethylethyl)-5-hydroxy-2-pyrimidine carboxaldehyde (1.5 g, 6.3 mmol), hydroxylamine hydrochloride (2.2 g, 32.7 mmol), and sodium acetate (2.9 g, 34.9 mmol) in ethanol (20 mL) is heated at reflux for 12 hours. The reaction mixture is poured over water (150 mL) and the precipitate is collected by filtration. Recrystallization from ether/hexane gives the desired 4,6-bis (1,1-dimethylethyl)-5-hydroxy-2-pyrimidine carboxaldehyde oxime as a mixture of isomers (0.62 g, 39%); mp 205°–220° C.

EXAMPLE 21

4,6-Bis(1,1-dimethylethyl)-5-hydroxy-2-pyrimidine carbothioamide

Hydrogen sulfide is bubbled through a solution of 4,6-bis (1,1-dimethylethyl)-5-hydroxy-2-pyrimidine carbonitrile (4.5 g, 19.3 mmol) and triethylamine (4.3 g, 42.4 mmol) in pyridine (20 ml) at room temperature for 6 hours. The reaction mixture is stirred at room temperature overnight. The solvent is evaporated under vacuum and the residue is recrystallized from ether/hexane to give pure 4,6-bis (1,1-dimethylethyl)-5-hydroxy-2-pyrimidine carbothioamide (3.0 g, 58%); mp 169°–171° C.

EXAMPLE 22

4,6-Bis(1,1-dimethylethyl)-5-hydroxy-2-pyrimidine carboxylic acid

A solution of 4,6-bis (1,1-dimethylethyl)-5-hydroxy-2-pyrimidine carboxylic acid methyl ester (500 mg) in 1N NaOH (50 mL) is heated at reflux for 1 hour. The reaction mixture is cooled, filtered, and acidified to pH 4 with 1N HCl. The resulting precipitate is collected by filtration and dried at room temperature under vacuum to give pure 4,6-bis(1,1-dimethylethyl)-5-hydroxy-2-pyrimidine carboxylic acid (430 mg); mp 200° C. dec.

EXAMPLE 23

5-[4,6-Bis(1,1-dimethylethyl)-5-hydroxy-2-pyrimidinyl]-2-methylsulfonyl-1,3,4-3H-thiadiazole m-Chloroperbenzoic acid (0.35 g, 2 mmol) is added in portions to a solution of 5-[4,6-bis(1,1-dimethylethyl)-5-hydroxy-2-pyrimidinyl]-2-thiomethoxy-1,3,4-3H-thiadiazole (0.23 g, 0.7 mmol) in methylene chloride (50 mL) at 0° C. The reaction mixture is stirred at 0° C. for 30 minutes and then at room temperature for 12 hours. The reaction mixture is washed with a saturated solution of sodium bicarbonate (3×50 mL) and dried over magnesium sulfate. Flash chromatography (silica; 50% ether/hexane) gives pure 5-[4,6-bis (1,1-dimethylethyl)-5-hydroxy-2-pyrimidinyl]-2-methylsulfonyl-1,3,4-3H-thiadiazole (0.13 g, 50%), mp 142°–144° C.

EXAMPLE 24

N-[5-[4,6-Bis(1,1-dimethylethyl)-5-hydroxypyrimidin-2-yl]-1,3,4-thiadiazol-2-yl]guanidine A mixture of sodium t-butoxide (1.8 mmol) and guanidine hydrochloride (0.2 g, 2.0 mmol) in t-butanol (15 mL) is stirred at room temperature for 1 hour. 5-[4,6-Bis(1,1-dimethylethyl)-5-hydroxy-2-pyrimidinyl]-2-methylsulfonyl-1,3,4-3H-thiadiazole (0.11 g, 0.3 mmol) is added and the reaction mixture is heated at reflux for 16 hours. The reaction mixture is cooled and the product is precipitated out with water. The pH of the resulting suspension is adjusted to pH 9 by the addition of 1N HCl and the precipitate is collected by filtration. Recrystallization from EtOAc gives 0.03 g (28%) of the desired N-[5-[4,6-bis(1,1-dimethylethyl)-5-hydroxypyrimidin- 2-yl]-1,3,4-thiadiazol-2-yl]guanidine, mp 277° C.

We claim:

1. A compound of the formula

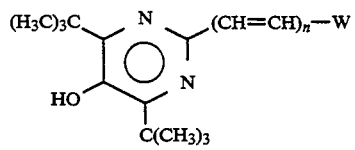

or a pharmaceutically acceptable acid addition or base salt thereof, and hydrates thereof; wherein n is an integer of zero or one;

W is

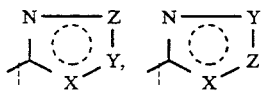

wherein X is O or S;
Z is NR$_1$ or N wherein R$_1$ is hydrogen or lower alkyl;
Y is (1) C—SR$_1$ wherein R$_1$ is independently as defined above,

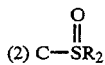

wherein R$_2$ is lower alkyl,

wherein R$_2$ is as defined above, (4) C—NR$_1$R$_3$ wherein R$_1$ is independently as defined above and R$_3$ is hydrogen or lower alkyl, (5) COR$_1$ wherein R$_1$ is independently as defined above, (6) CR$_4$ wherein R$_4$ is halogen, CF$_3$, CO$_2$R$_1$, or

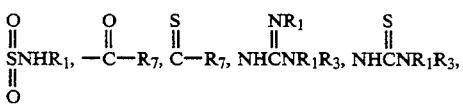

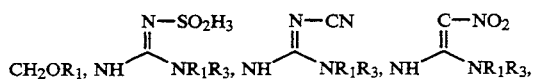

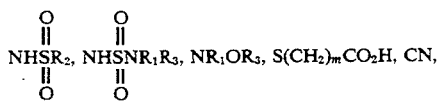

NH(CH$_2$)$_m$OH, CCl$_3$, CONR$_1$R$_3$, CSNR$_1$R$_3$, CH$_2$X$_{10}$,

CH$_2$NR$_{11}$R$_{13}$, NHCSNHCO$_2$R$_2$, CH$_2$SR$_2$, CH$_2$SO$_2$R$_2$, or

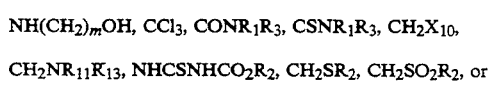

NHNH$_2$, (7)

wherein m is 1,2 or 3; R$_{11}$ and R$_{13}$ are hydrogen or lower alkyl; X$_{10}$ is halogen or NO$_2$; R$_5$ is H, lower alkyl or OR$_1$, R$_7$ is lower alkyl, phenyl, or CF$_3$; and R$_1$, R$_2$, and R$_3$ are independently as defined above.

2. A compound of claim 1 wherein W is

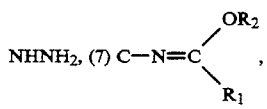

wherein X is S, and n, Z and Y are as defined above.
3. A compound of claim 2 wherein n is zero.
4. A compound of claim 2 wherein n is one.
5. A compound of claim 1 wherein W is

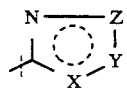

wherein X is O and n, Z, and Y are as defined above.
6. A compound of claim 5 wherein n is zero.
7. A compound of claim 5 wherein n is one.
8. A compound of claim 1 wherein W is

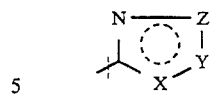

wherein Z is N and and Y are as defined above.
9. A compound of claim 8 wherein n is zero.
10. A compound of claim 8 wherein n is one.
11. A compound of claim 1 wherein W is

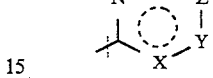

wherein X is S, and n, Z, and Y are as defined above.
12. A compound of claim 11 wherein n is zero.
13. A compound of claim 11 wherein n is one.
14. A compound of claim 1 wherein W is

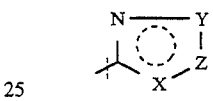

wherein X is O and n, Z, and Y are as defined above.
15. A compound of claim 14 wherein n is zero.
16. A compound of claim 14 wherein n is one.
17. A compound of claim 3 which is 5-[4,6-bis(1,1-dimethylethyl)-5-hydroxypyrimidinyl]-2H-1,3,4-thiadiazole-2-thione.
18. A compound of claim 1 selected from the group consisting of
  5-[4,6-bis(1,1-dimethylethyl)-5-hydroxy-2-pyrimidinyl]-1,3,4-oxadiazole-2 (3H)-one,
  5-[4,6-bis(1,1-dimethylethyl)-5-hydroxy-2-pyrimidinyl]-1,3,4-oxadiazole-2 (3H)-thione,
  5-[4,6-bis(1,1-dimethylethyl)-5-hydroxy-2-pyrimidinyl]-2-thiomethoxy-1,3,4-3H-thiadiazole,
  5-[4,6-bis(1,1-dimethylethyl)-5-hydroxy-2-pyrimidinyl]-2-methylsulfonyl-1,3,4-3H-thiadiazole, and
  N-[5-[4,6-bis(1,1-dimethylethyl)-5-hydroxy-pyrimidinyl-2-yl]-1,3,4-thiadiazol-2-yl]guanidine.
19. A pharmaceutical composition for the treatment of a condition advantageously affected by the inhibition of 5-lipoxygenase, cyclooxygenase or both 5-lipoxygenase and cyclooxygenase which comprises an amount effective for the treatment of the condition of the compound of claim 1 and a pharmaceutically acceptable carrier.
20. A method of treating inflammation in a human in need of such treatment which comprises administering a compound of claim 1 in unit dosage form.
21. A method of treating allergy in a human in need of such treatment which comprises administering a compound of claim 1 in unit dosage form.

22. A method of treating ulcers in a human in need of such treatment which comprises administering a compound of claim 1 in unit dosage form.

23. A pharmaceutical con, position which comprises a compound of formula I and a nonsteroidal antiinflammatory drug in an amount wherein a ratio of the weight range is from 1000:1 to 1:1000.

24. A compound of the formula III

Q'At'Q"    III wherein Ar' is a group of the formula

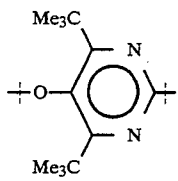

Me is $CH_3$;

Q' is hydrogen or a hydroxy protecting group;

Q" is —CHNOH, —CN, —$CO_2H$, —$CSNH_2$ or

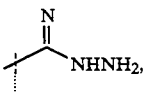

CHO, —$COOR_{20}$ wherein $R_{20}$ is lower alkyl.

25. A compound of claim 24 which is
4,6-Bis(1,1-dimethylethyl)-5-[(2-methoxyethoxy)methoxy]-2-pyrimidinecarbonitrile
4,6-Bis(1,1-dimethylethyl)-5-hydroxy-2-pyrimidinecarbonitrile;
4,6-Bis(1,1-dimethylethyl)-5-[(2-methoxyethoxy)methoxy]-2-pyrimidinecarboxaldehyde oxime;
4,6-Bis(1,1-dimethylethyl)-5-hydroxy-2-pyrimidinecarboxaldehyde oxime;
4,6-Bis(1,1-dimethylethyl)-5-[(2-methoxyethoxy)methoxy]-2-pyrimidinecarbothioamide
4,6-Bis(1,1-dimethylethyl)-5-hydroxy-2-pyrimidinecarbothioamide;
4,6-Bis(1,1-dimethylethyl)-5-hydroxy-2-pyrimidine carboxaldehyde;
4,6-Bis(1,1-dimethylethyl)-5-[(2-methoxyethoxy)methoxy]-2-pyrimidine carboxaldehyde
4,6-Bis(1,1-dimethylethyl)-5-hydroxy-2-pyrimidine carboxylic acid;
4,6-Bis(1,1-dimethylethyl)-5-hydroxy-2-pyrimidine carboxylic acid methyl ester; and
4,6-Bis(1,1-dimethylethyl)-5-[(2-methoxyethoxy)methoxy]-2-pyrimidine carboxylic acid methyl ester.

* * * * *

UNITED STATES PATENT AND TRADEMARK OFFICE
CERTIFICATE OF CORRECTION

PATENT NO. : 5,356,898
DATED : October 18, 1994
INVENTOR(S) : Belliotti et al.

It is certified that error appears in the above-identified patent and that said Letters Patent is hereby corrected as shown below:

Column 37,
Line 35,

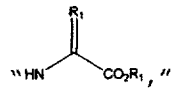

Should read
- -

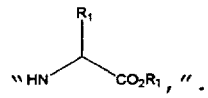

- -

Column 38,
Line 17, insert "n" between "and" and "and".

Column 39,
Line 6, "con position" should read "composition".
Line 14, "Q'At'Q" should read "Q'Ar'Q".

Signed and Sealed this

Twenty-third Day of October, 2001

Attest:

*Nicholas P. Godici*

NICHOLAS P. GODICI
*Attesting Officer*    *Acting Director of the United States Patent and Trademark Office*